(12) United States Patent
Baker et al.

(10) Patent No.: US 7,923,528 B2
(45) Date of Patent: Apr. 12, 2011

(54) DEGRADABLE 1,4-BENZODIOXEPIN-3-HEXYL-2,5-DIONE MONOMER DERIVED POLYMER WITH A HIGH GLASS TRANSITION TEMPERATURE

(75) Inventors: Gregory L. Baker, Haslett, MI (US); Feng Jing, Saint Paul, MN (US); Milton R. Smith, III, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 476 days.

(21) Appl. No.: 11/980,209

(22) Filed: Oct. 30, 2007

(65) Prior Publication Data

US 2008/0146774 A1 Jun. 19, 2008

Related U.S. Application Data

(60) Provisional application No. 60/855,723, filed on Oct. 31, 2006.

(51) Int. Cl.
*C08G 63/08* (2006.01)

(52) U.S. Cl. ........................................ 528/354; 528/480

(58) Field of Classification Search ................. 528/354, 528/480
See application file for complete search history.

(56) References Cited

U.S. PATENT DOCUMENTS 5,082,925 A * 1/1992 Shalaby et al. ............... 528/354
2001/0009662 A1 7/2001 Cohn et al.

OTHER PUBLICATIONS

Dechy-Cabaret, O.; Martin-Vaca, B.; Bourissou, D. Chem. Rev. 2004, 104, 6147-6176.
Lenz, R. W.; Marchessault, R. H. Biomacromolecules 2005, 6, 1-8.
Mecking, S. Angewandte Chemie-International Edition 2004, 43, 1078-1085.
Kint, D. P. R.; Munoz-Guerra, S. Polym. Int. 2003, 52, 321-336.
Nagahata, R.; Sugiyama, J.; Goyal, M.; Asai, M.; Ueda, M.; Takeuchi, K. J. Polym. Sci., Part A: Polym. Chem. 2000, 38, 3360-3368.
Nagahata, R.; Sugiyama, J. J.; Goyal, M.; Goto, M.; Honda, K.; Asai, M.; Ueda, M.; Takeuchi, K. Polymer 2001, 42, 1275-1279.
Youk, J. H.; Boulares, A.; Kambour, R. P.; MacKnight, W. J. Macromolecules 2000, 33, 3600-3605.
Schmeltzer, R. C.; Schmalenberg, K. E.; Uhrich, K. E. Biomacromolecules 2005, 6, 359-367.
Prudencio, A.; Schmeltzer, R. C.; Uhrich, K. E. Macromolecules 2005, 38, 6895-6901.
Schmeltzer, R. C.; Anastasiou, T. J.; Uhrich, K. E. Polym. Bull. 2003, 49, 441-448.
Anastasiou, T. J.; Uhrich, K. E. J. Polym. Sci., Part A: Polym. Chem. 2003, 41, 3667-3679.
Bedell, C.; Deng, M.; Anastasiou, T. J.; Uhrich, K. E. J. Appl. Polym. Sci. 2001, 80, 32-38.
Auras, R.; Harte, B.; Selke, S. Macromol. Biosci. 2004, 4, 835-864.
Liu, T. Q.; Simmons, T. L.; Baker, G. L. Polymeric Materials: Science & Engineering 2003, 88, 420.
Jing, F.; Smith, M. R.; Baker, G. L. Polym. Prepr. 2005, 46, 1006.
Kagan, F.; Birkenmeyer, R. D. J. Am. Chem. Soc. 1959, 81, 1986-1991.
A. Duda, A. Kowalski, J. Libiszowski, and S. Penczek, Macromol. Symp. 2005, 224, 71-83.
Fan, Y. J.; Nishida, H.; Shirai, Y.; Endo, T. Polym. Degrad. Stab. 2004, 84, 143.
Nishida, H.; Mori, T.; Hoshihara, S.; Fan, Y. J.; Shirai, Y.; Endo, T. Polym. Degrad. Stab. 2003, 81, 515.
Nederberg, F.; Connor, E. F.; Glausser, T.; Hedrick, J. L. Chem. Commun. 2001, 2066-2067.
Nederberg, F.; Connor, E. F.; Moller, M.; Glauser, T.; Hedrick, J. L. Angewandte Chemie-International Edition 2001, 40, 2712-2715.
Witzke, D. R.; Narayan, R.; Kolstad, J. J. Macromolecules 1997, 30, 7075-7085.
Yin, M.; Baker, G. L. Macromolecules 1999, 32, 7711-7718.
Aggarwal, V.K.; Thomas, A.; Schade, S. Tetrahedron 1997, 53, 16213-16228.
Masamune, S.; Choy, W.; Kerdesky, F.A.J.; Imperiali, B. Journal of the American Chemical Society 1981, 103, 1566-1568.
Kowalski, A. et al., "Kinetics and Mechanism of Cyclic Esters Polymerization Initiated with Tin(II) Octoate. 3. Polymerization of L,L-Dilactide" Macromolecules (2000), 33, 7359-7370.
Liu, T. et al., "Synthesis of Polymandelide: A Degradable Polylactide Derivative with Polystyrene-like Properties" Macromolecules (2007), 40, 6040-6047.
International Search Report for PCT/US07/22888 (International Filing Date of Oct. 30, 2007) with a mailing date of Mar. 17, 2008.

* cited by examiner

*Primary Examiner* — David Wu
*Assistant Examiner* — Gregory Listvoyb
(74) *Attorney, Agent, or Firm* — Ian C. McLeod; Steven M. Park

(57) ABSTRACT

A homopolymer of 1,4-benzodioxepin-3-cyclohexyl-2,5-dione with a $T_g$ of 120° C. Copolymers are also described. The polymers are useful for surgical and other applications where biodegradability is important.

3 Claims, 18 Drawing Sheets

R = methyl
= cyclohexyl 1,4-benzodioxepin-3-methyl-2,5-dione poly(1,4-benzodioxepin-3-methyl-2,5-dione)

Supporting Iformation

DEGRADABLE 1,4-BENZODIOXEPIN-3-HEXYL-2,5-DIONE MONOMER DERIVED POLYMER WITH A HIGH GLASS TRANSITION TEMPERATURE

CROSS-REFERENCE TO RELATED APPLICATIONS

This application claims benefit to U.S. Provisional Application Ser. No. 60/855,723, filed Oct. 31, 2006, which is incorporated herein by reference in its entirety.

STATEMENT REGARDING FEDERALLY SPONSORED RESEARCH OR DEVELOPMENT

Not Applicable.

REFERENCE TO A "COMPUTER LISTING APPENDIX SUBMITTED ON A COMPACT DISC"

Not Applicable.

BACKGROUND OF THE INVENTION (1) Field of the Invention

The present invention relates to a degradable 1,4-benzodioxepin-3-hexyl-2,5-dione monomer derived polymer. The homopolymer has a high glass transition temperature. Also, the invention relates to heteropolymers from this monomer.

(2) Description of Related Art

In the discovery and development of biodegradable plastics, aliphatic polyesters, such as polylactide ([1]Dechy-Cabaret, O.; Martin-Vaca, B.; Bourissou, D. *Chem. Rev.* 2004, 104, 6147-6176) and poly(3-hydroxybutyrate); and ([2]Lenz, R. W.; Marchessault, R. H. *Biomacromolecules* 2005, 6, 1-8), have played a key role ([3]Mecking, S. *Angewandte Chemie-International Edition* 2004, 43, 1078-1085). However, modern polyester industry is still dominated by aromatic polyesters, e.g. poly(ethylene terephalate) (PET) and poly(butylene terephthalate) (PBT), because of their excellent thermal and mechanical properties, high chemical resistance and extremely low gas permeability. Now, the relative stability and biological inertness of these aromatic polyesters are becoming a major drawback, especially in the area of disposable materials, such as widely used non-degradable PET-based beverage bottles. According to EPA, in 2003 only 5.2% of rubber in municipal solid waste was recovered in the United States in 2003.

In an attempt to combine the excellent material properties of aromatic polyesters with the potential biodegradability of aliphatic polyesters, a number of aliphatic-aromatic polyesters have been developed. For example, both BASF and Eastman Chemical are currently marketing biodegradable polyesters of terephthalic acid and adipic acid with 1,4-butanediol under the trade names of Ecoflex™ and Eastar Bio™, respectively. Generally, aliphatic-aromatic polyester is made by copolymerizing aromatic diacid (mostly terephthalic acid) and aliphatic diacid (adipic acid, sebacic acid, or fumaric acid) with aliphatic diol (ethylene glycol, PEG-diol, or 1,4-cyclohexanedimethanol) via polycondensation reaction.

However, incorporating flexible aliphatic ester chains into rigid aromatic polyesters to introduce degradability greatly reduces $T_g$ and $T_m$. Compared to PET ($T_g=78°$ C., $T_m=260°$ C.), ([4]Kint, D. P. R.; Munoz-Guerra, S. *Polym. Int.* 2003, 52, 321-336) Ecoflex has much lower $T_g$ ($-30°$ C.) and $T_m$ (110-115° C.), ([3]Mecking, S. *Angewandte Chemie-International Edition* 2004, 43, 1078-1085). As a result, the use temperatures of aliphatic-aromatic polyesters are severely compromised, and their low $T_g$ and high crystallinity will inevitably limit their uses as rigid, clear replacements for large-volume thermoplastics such as polystyrene. Furthermore, the polycondensation reaction applied in synthesizing aliphatic-aromatic polyester is accompanied by low molecular weight, high polydispersity, and poor regioselectivity control of the polymer structure.

Although the ring-opening polymerization of cyclic oligomers to form PET has been realized, ([5]Nagahata, R.; Sugiyama, J.; Goyal, M.; Asai, M.; Ueda, M.; Takeuchi, K. J. *Polym. Sci., Part A: Polym. Chem.* 2000, 38, 3360-3368); ([6]Nagahata, R.; Sugiyama, J. J.; Goyal, M.; Goto, M.; Honda, K.; Asai, M.; Ueda, M.; Takeuchi, K. *Polymer* 2001, 42, 1275-1279); ([7]Youk, J. H.; Boulares, A.; Kambour, R. P.; MacKnight, W. J. *Macromolecules* 2000, 33, 3600-3605), aliphatic-aromatic polyester synthesized by ring-opening polymerization is very rare. An exceptional way of mimicking aliphatic-aromatic polyester with better thermal stability but also utilizing ring-opening polymerization to fine control the polymer structure was patented (U.S. Pat. No. 5,082,925 to Shalaby et al) (Scheme 1) (Shalaby, S. W.; Koelmel, D. F.; Arnold, S. U.S. Pat. No. 5,082,925 (1992)). In vitro and in vivo degradations showed that this polymer is completely biodegradable.

Scheme 1

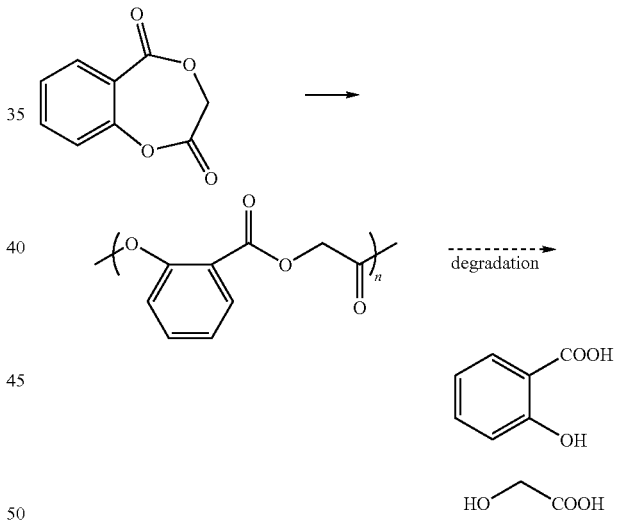

wherein R is hydrogen or methyl

Scheme 1. Synthesis and degradation of poly(1,4-benzodioxepin-2,5(3H)-dione) and poly(1,4-benzodioxepin-2,5(3H)-3-methyl-dione.

Another important feature of poly(1,4-benzodioxepin-2,5 (3H)-dione) is that its degradation releases therapeutically active salicylic acid, as does aspirin. In this aspect, it shows very similar feature as that of well-studied salicylate-based poly(anhydride esters). ([8]Schmeltzer, R. C.; Schmalenberg, K. E.; Uhrich, K. E. *Biomacromolecules* 2005, 6, 359-367); ([9]Prudencio, A.; Schmeltzer, R. C.; Uhrich, K. E. *Macromolecules* 2005, 38, 6895-6901); ([10]Schmeltzer, R. C.; Anastasiou, T. J.; Uhrich, K. E. *Polym. Bull.* 2003, 49, 441-448); ([11]Anastasiou, T. J.; Uhrich, K. E. *J. Polym. Sci., Part A: Polym. Chem.* 2003, 41, 3667-3679); and ([12]Bedell, C.; Deng, M.; Anastasiou, T. J.; Uhrich, K. E. *J. Appl. Polym. Sci.* 2001, 80, 32-38). In both cases drug is released upon the hydrolysis of the polymer backbone, and degradation profiles, as well as physical properties such as $T_g$, can be manipulated by incorporating different linkers. See references: ([13]Auras, R.; Harte, B.; Selke, S. *Macromol. Biosci.* 2004, 4, 835-864); ([14]Liu, T. Q.; Simmons, T. L.; Baker, G. L. Polymeric Materials: Science & Engineering 2003, 88, 420); ([24]Aggarwal, V. K.; Thomas, A.; Schade, S. Tetrahedron 1997, 53, 16213-16228); ([25]Masamune, S.; Choy, W.; Kerdesky, F. A. J.; Imperiali, B. Journal of the American Chemical Society 1981, 103, 1566-1568).

OBJECTS

It is therefore an object of the present invention to provide a biodegradable poly(1,4-benzodioxepin-3-hexyl-2,5-dione. It is further an object to provide a polymer with a relatively high glass transition temperature. Further, it is an object of the present invention to provide a polymer which is economical. These and other objects will become increasingly apparent by reference to the following drawings.

SUMMARY OF THE INVENTION

The present invention relates to a homopolymer of a monomer represented by the following formula:

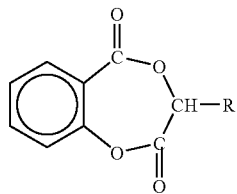

The glass transition temperature of the homopolymer is about 120° C.

The present invention also relates to the monomer represented by the formula above and at least one of the following comonomers: a) glycolide, b) (L)-lactide, c) an alkylene carbonate, d) p-dioxanone, e) ε-caprolactone, f) 1,4-dioxepan-2-one, or g) 1,5-dioxepan-2-one. Preferably the comonomer is glycolide or L-lactide. Most preferably the comonomer is glycolide. Most preferably the amount of the monomer represented by the formula above ranges from about 1 to about 35 weight percent. Most preferably the amount of the monomer represented by the formula above ranges from about 5 to about 15 weight percent. Preferably, a surgical device is prepared from the homopolymer. Also preferably, wherein a surgical device prepared from the copolymer.

DESCRIPTION OF THE PREFERRED EMBODIMENTS

Figure 1:
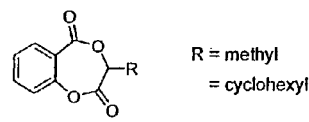
FIG. 1 are structures of 1,4-benzodioxepin-3-hexyl-2,5-dione and 1,4-benzodioxepin-3-methyl dione.

The $T_g$ of polylactide, the thermal and mechanical properties of poly(1,4-benzodioxepin-2,5(3H)-dione) can be enhanced by introducing a bulky side chain to the glycolic acid repeating units. By varying the substituent R to cyclohexyl (FIG. 1) and/or stereochemistry, the crystallinity and the rigidity of polymer chain can be manipulated. In this invention, cyclohexyl groups were added to the monomer to racemic 1,4-benzodioxepin-3-hexyl-2,5-dione. In this way, the polymer rigidity is enhanced and crystallinity is eliminated by the random distribution of chiral centers, thus providing amorphous, high $T_g$ polyesters with improved thermal and mechanical properties.

Poly(1,4-benzodioxepin-2,5(3H)-dione) by comparison is semi-crystalline and its $T_g$ and $T_m$ range from 57-73° C. and 165-168° C., respectively (Shalaby, S. W.; Koelmel, D. F.; Arnold, S. U.S. Pat. No. 5,082,925 (1992)).

Synthesis of 1,4-benzodioxepin-3-alkyl-2,5-diones 1,4-benzodioxepin-3-methyl-2,5-dione of the prior art and 1,4-benzodioxepin-3-cyclohexyl-2,5-dione shown in Scheme 2 and Scheme 3 respectively were synthesized using the reported synthetic protocols (Shalaby, S. W.; Koelmel, D. F.; Arnold, S. U.S. Pat. No. 5,082,925 (1992)); and ([16]Kagan, F.; Birkenmeyer, R. D. *J. Am. Chem. Soc.* 1959, 81, 1986-1991).

Scheme 2. Synthetic route to 1,4-benzodioxepin-3-methyl-2,5-dione

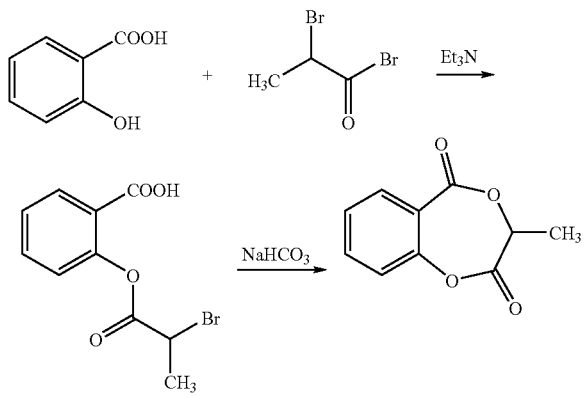

(Scheme 3), different side chains can be attached to the 7-membered lactone ring, which will in turn bring the polymers with tailored physical properties.

Figure 2A:
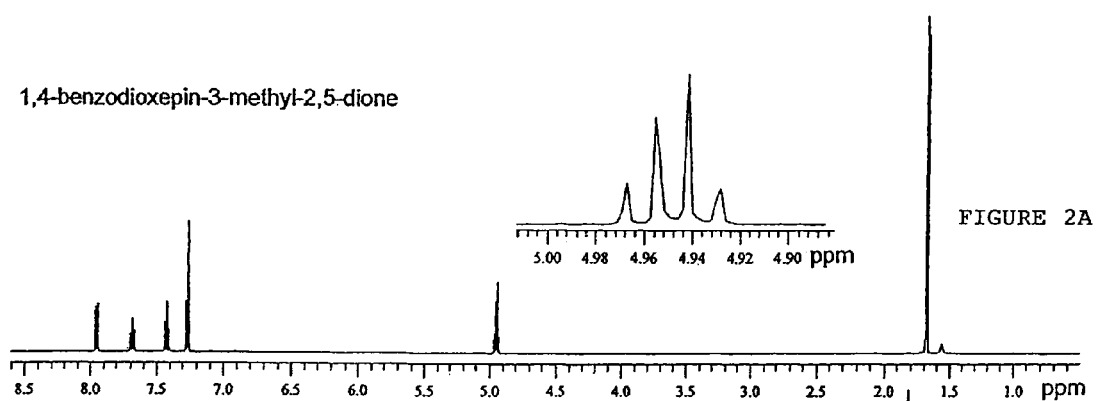
FIGS. 2A and 2B are graphs showing 500 MHz $^1$H NMR spectra of 1,4-benzodioxepin-3-methyl-2,5-dione (FIG. 2A) and its polymer (FIG. 2B).
Figure 2B:
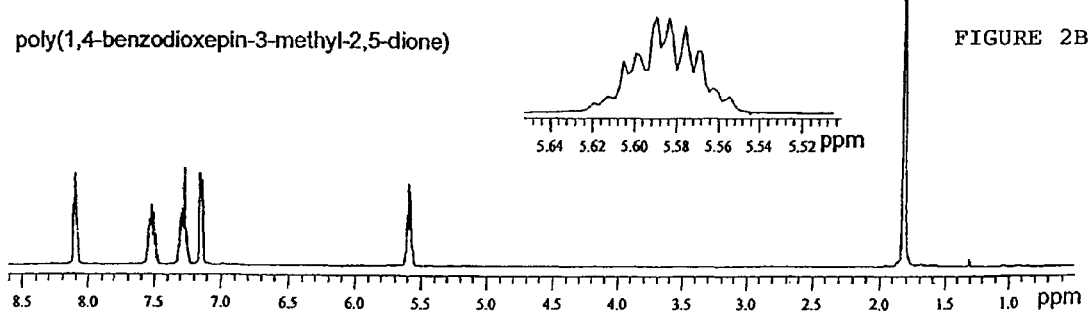

The ring-opening polymerization of 1,4-benzodioxepin-3-methyl-2,5-dione was catalyzed by Sn(2-ethylhexanoate)$_2$ using 4-tert-butylbenzyl alcohol as the initiator. The $^1$H NMR spectra of the monomer and the polymer are shown in FIGS. 2A and 2B and the characterization data for the polymer are listed in Table 1.

TABLE 1

| Characterization of poly(1,4-benzodioxepin-3-methyl-2,5-dione) | | |
|---|---|---|
| $M_n$ | $M_w/M_n$ | $T_g$(° C.) |
| 22,700 | 1.86 | 92 |

Ring-opening Regioselectivity. Tin(II) 2-ethylhexanoate, one of the most used organometallic catalysts for cyclic lactones, was initially used to catalyze the ring-opening polymerization. Although the solution and bulk polymerization of 1,4-benzodioxepin-3-methyl-2,5-dione were successful, the bulk polymerization rate of 1,4-benzodioxepin-3-cyclohexyl-2,5-dione was very slow: the conversion was less than 5% after 1 hour at 160° C. with a 1 mol % loading ratio of tin(II) 2-ethylhexanoate and 4-tert-butylbenzyl alcohol. This is probably due to the moderate ring strain of the 7-membered lactone ring, ([17]A. Duda, A. Kowalski, J. Libiszowski, and S. Penczek, *Macromol. Symp.* 2005, 224, 71-83) the high steric Scheme 3. Synthetic route to 1,4-benzodioxepin-3-cyclohexyl-2,5-dione

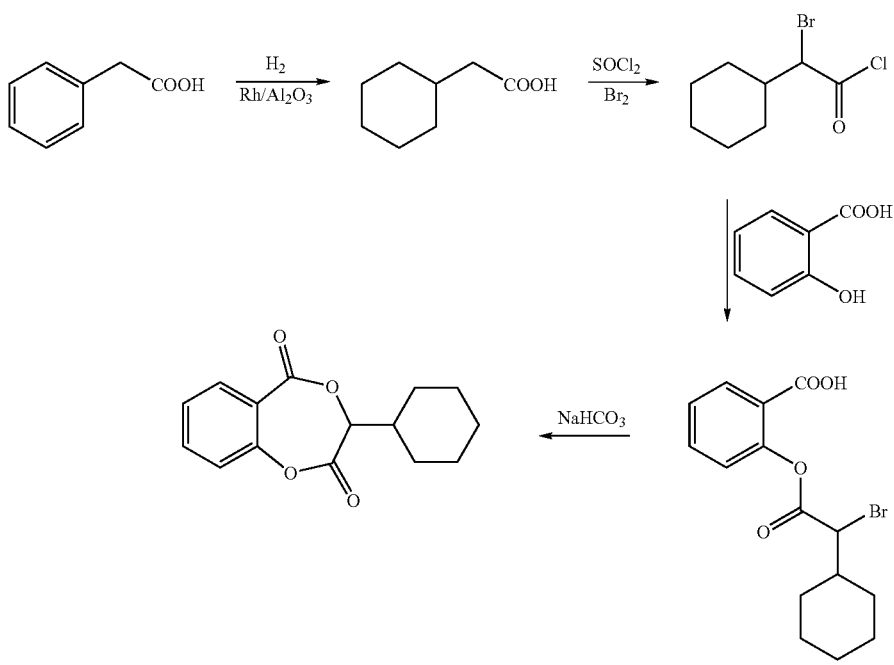

The synthesis starts from the coupling reaction between salicylic acid and the corresponding α-bromo acid bromide/chloride, followed by the intramolecular cyclization of the linear intermediate catalyzed by weak inorganic base NaHCO$_3$ in acetone. By applying various commercial available α-bromo acid halides (Scheme 2) or making them via α-bromination from the corresponding carboxylic acids hindrance imposed by the bulky cyclohexyl ring, ([15]Jing, F.; Smith, M. R.; Baker, G. L. *Polym. Prepr.* 2005, 46, 1006), and the insufficiently activated carboxyl group(s) by tin(II) 2-ethylhexanoate. Another side effect of using tin(II) 2-ethylhexanoate is the difficulty of removing the catalyst even through repeated precipitation process, ([18]Fan, Y. J.; Nishida, H.; Shirai, Y.; Endo, T. *Polym. Degrad. Stab.* 2004, 84, 143), the result of which would lead to faster but unpredictable degradation profile ([19]Nishida, H.; Mori, T.; Hoshihara, S.; Fan, Y. J.; Shirai, Y.; Endo, T. *Polym. Degrad. Stab.* 2003, 81, 515). To avoid the contamination from organometallic catalyst and fasten the polymerization, 4-(dimethylamino)pyridine (DMAP) and 1-phenylethanol, which were first used by Hedrick and his coworkers to successfully polymerize lactide, ([20]Nederberg, F.; Connor, E. F.; Glausser, T.; Hedrick, J. L. *Chem. Commun.* 2001, 2066-2067); and ([21]Nederberg, F.; Connor, E. F.; Moller, M.; Glauser, T.; Hedrick, J. L. *Angewandte Chemie-International Edition* 2001, 40, 2712-2715), were chosen as the catalyst and initiator respectively for the ring-opening polymerization of 1,4-benzodioxepin-3-alkyl-2,5-diones. Representative $^1$H NMR spectra of 1,4-benzodioxepin-3-cyclohexyl-2,5-dione and its polymer are shown in FIGS. 2A and 2B. The $^1$H NMR spectrum of the monomer shows the expected doublet for the methine protons at 4.40 ppm. After polymerization, the signals from the methine protons broaden and shift downfield to 5.27-5.37 ppm, allowing simple calculation of conversion from the integrated intensities of the monomer and polymer methine signals.

Scheme 4. Pathways of ROP of 1,4-benzodioxepin-3-alkyl-2,5-diones

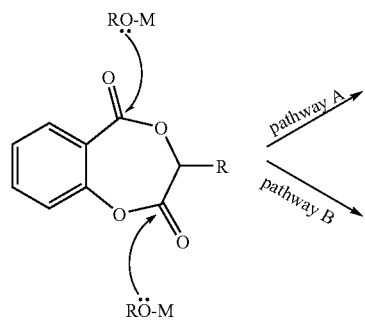

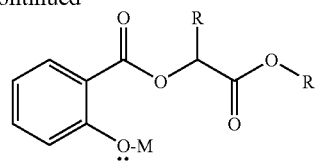

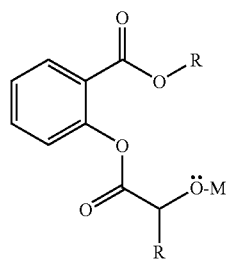

Figure 3:
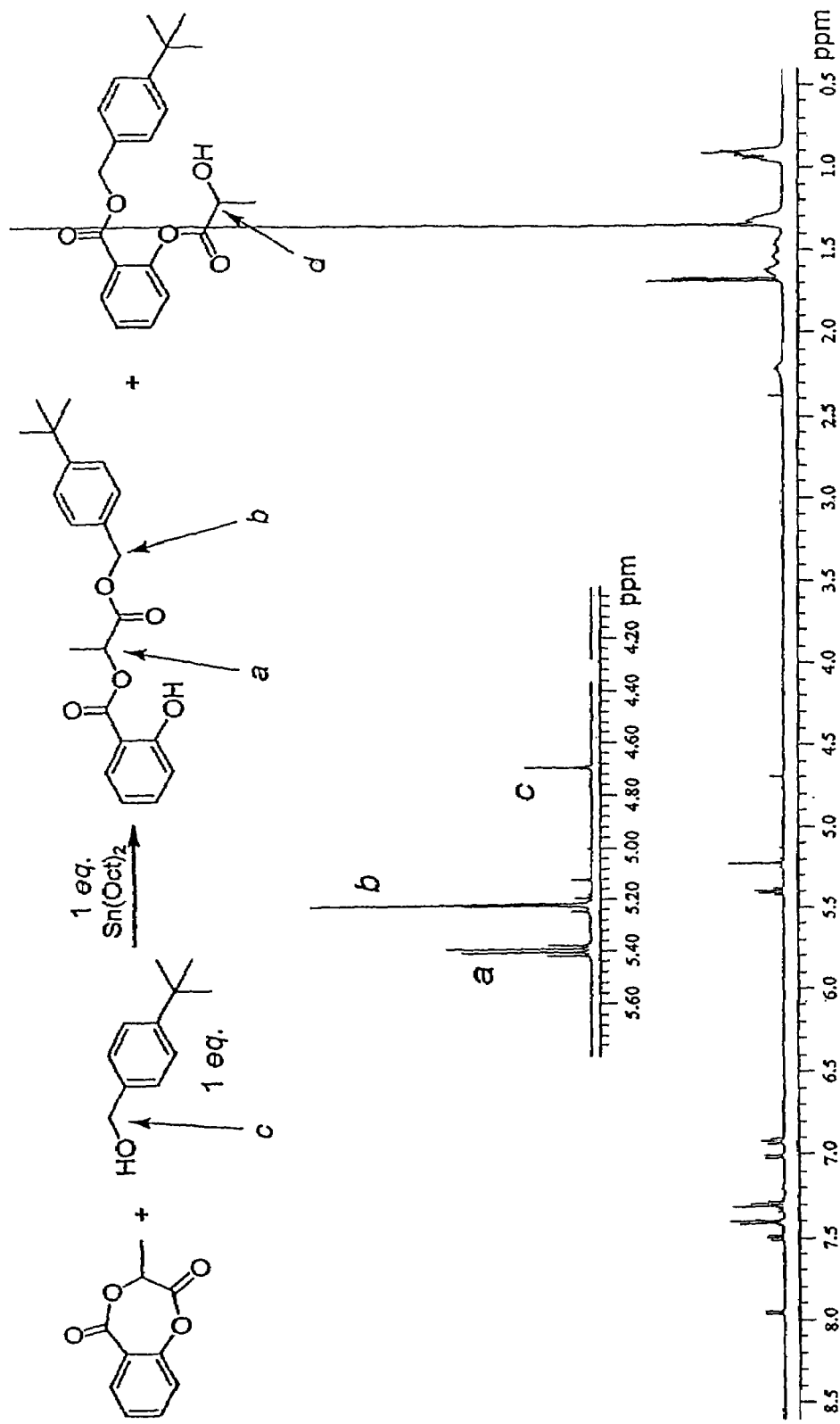
FIG. 3 is a graph showing 500 MHZ $^1$H NMR spectrum of 1,4-benzodioxepin-3-methyl-2,5-dione ring-opened product by Sn(2-ethylhexanoate)$_2$ and 4-tert-butylbenzyl alcohol.
Figure 4:
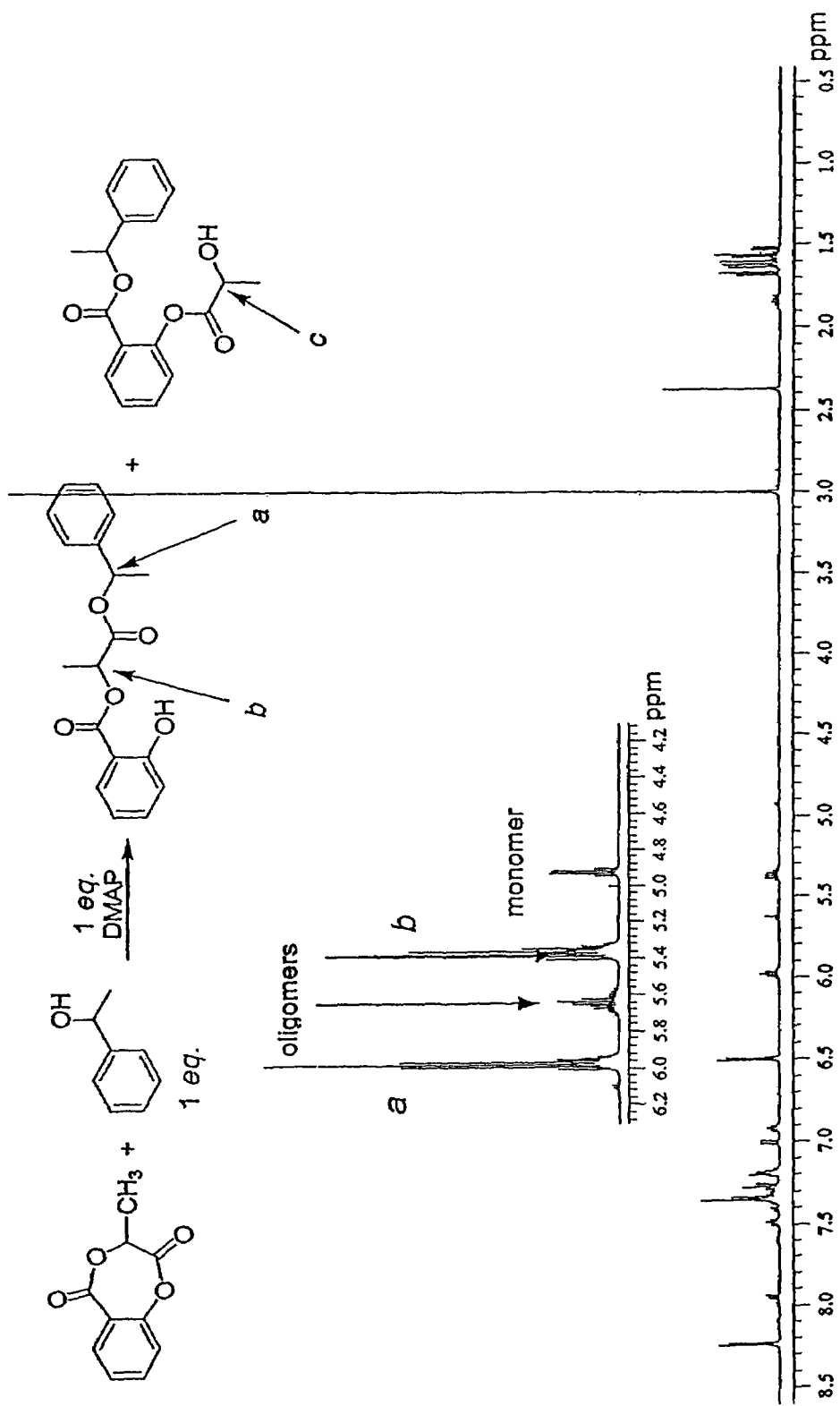
FIG. 4 is a graph showing 500 MHz $^1$H NMR spectrum of 1,4-benzodioxepin-3-methyl-2,5-dione ring-opened product by DMAP and 1-phenylethanol.
Figure 5:
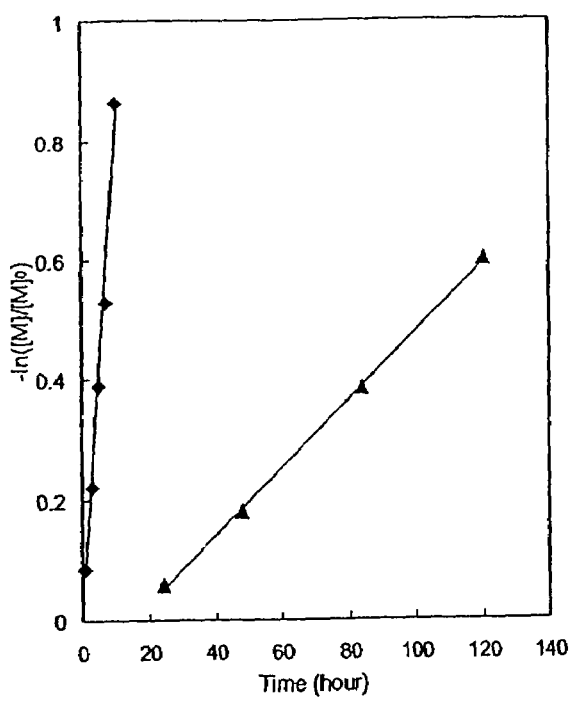
FIG. 5 is a graph showing solution polymerization kinetics of 1,4-benzodioxepin-3-methyl-2,5-dione (♦) and 1,4-benzodioxepin-3-cyclohexyl-2,5-dione (▲). Polymerization conditions: 90° C., [monomer]:[DMAP]:[1-phenylethanol]= 100:2:1.

Unlike racemic lactide, racemic 1,4-benzodioxepin-3-alkyl-2,5-dione has two different carboxyl groups, the ring-opening of which leads to different polymer sequences along with different end groups (alcohol vs. phenol). Before unveiling the polymerization mechanism, we must answer one question: which ester is preferentially or exclusively opened when using DMAP as the catalyst and 1-phenylethanol as the initiator (pathway A and B in Scheme 4)? To answer this question, 1,4-benzodioxepin-3-methyl-2,5-dione was reacted with 2 equivalents of DMAP and 1 equivalent of 1-phenylethanol, and the final product (without purification) was analyzed by $^1$H NMR. As shown in FIG. 3, there was no noticeable product formed via pathway B, and the ring-opening reaction proceeded almost exclusively by pathway A.

Based on this result, the plausible mechanism of the ring-opening polymerization of 1,4-benzodioxepin-3-alkyl-2,5-dione catalyzed by DMAP and alcohol is shown in Scheme 5 ([21]Nederberg, F.; Connor, E. F.; Moller, M.; Glauser, T.; Hedrick, J. L. *Angewandte Chemie-International Edition* 2001, 40, 2712-2715).

Scheme 5. Mechanism of ROP of lactide initiated by DMAP and Alcohol

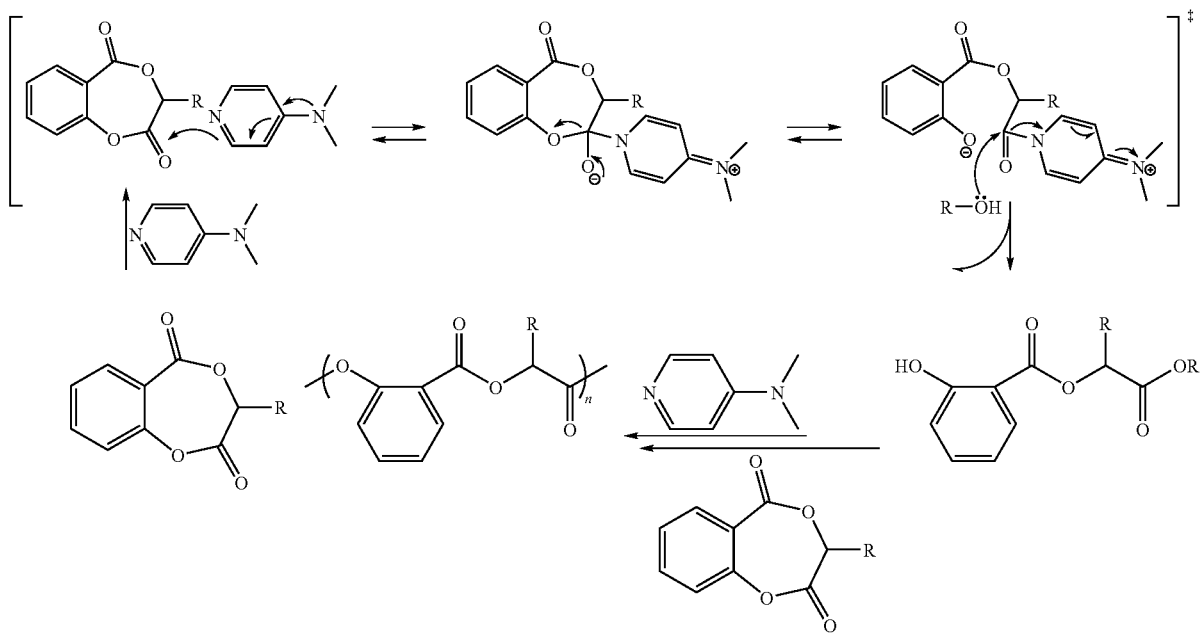

Solution polymerization kinetics. Solution polymerizations of 1,4-benzodioxepin-3-methyl-2,5-dione and 1,4-benzodioxepin-3-cyclohexyl-2,5-dione using DMAP as the catalyst and 1-phenylethanol as the initiator were carried out in toluene to evaluate the effect of the size of alkyl substituents on the rate of polymerization.

While the ring-opening polymerization of lactide catalyzed by DMAP and alcohol was proven to be a living polymerization, ([21]Nederberg, F.; Connor, E. F.; Moller, M.; Glauser, T.; Hedrick, J. L. *Angewandte Chemie-International Edition* 2001, 40, 2712-2715), no experiment has been done so far to reveal the polymerization kinetics. As shown in Scheme 5, if the formation of monomer-DMAP complex is under equilibrium, the rate-limiting step will be the addition of alcohol to the monomer-DMAP complex. So the ring-opening polymerization can be treated as a first-order reaction when the concentrations of catalyst and initiator stay constant. To test this assumption, solution polymerizations were run under low conversions and at low concentration.

For polymerizations at 90° C. with relatively low monomer concentrations (~0.2 M) and initiator and catalyst loadings (≦2 mol %), conversion is easily controlled, depolymerization is negligible, and the polymerization can be treated as an irreversible reaction ([22]Witzke, D. R.; Narayan, R.; Kolstad, J. J. *Macromolecules* 1997, 30, 7075-7085), as expressed in equation 1:

$$R = -\frac{d[M]}{dt} = k_p[M][I] \quad (1)$$

where [M] and [I] are the concentration of monomer and initiator respectively, and $k_p$ is the apparent rate constant for propagation. For a living polymerization, [I] is a constant, and plots of $-\ln([M]_t/[M]_0)$ versus time t should be linear with slope $k_p[I]$, where $[M]_t$ is the concentration of the monomer at time t and $[M]_0$ is the initial monomer concentration.

The data shown in FIG. 3 are consistent with first-order kinetics. As expected, the polymerization rates (Table 1) depend on the size of the alkyl substituents, with $k_p$ of 1,4-benzodioxepin-3-cyclohexyl-2,5-dione being $1/15^{th}$ of 1,4-benzodioxepin-3-methyl-2,5-dione.

TABLE 2

Solution polymerization rates of 1,4-benzodioxepin-3-alkyl-2,5-diones

| Monomer | $k_p$ (L · s$^{-1}$ · mol$^{-1}$) × 10$^6$ |
|---|---|
| 1,4-benzodioxepin-3-methyl-2,5-dione | 118 |
| 1,4-benzodioxepin-3-cyclohexyl-2,5-dione | 7.78 |

Bulk polymerization kinetics. The kinetic behaviors of bulk polymerizations of the prior art of 1,4-benzodioxepin-3-methyl-2,5-dione and 1,4-benzodioxepin-3-cyclohexyl-2,5-dione were examined at 130° C. and 160° C. respectively. The monomer, 2 mol % DMAP, and 1 mol % 1-phenylethanol were loaded into glass tubes and the tubes were sealed under vacuum. The tubes were immersed in oil bath at predetermined temperature and removed at desired times.

Figure 6:
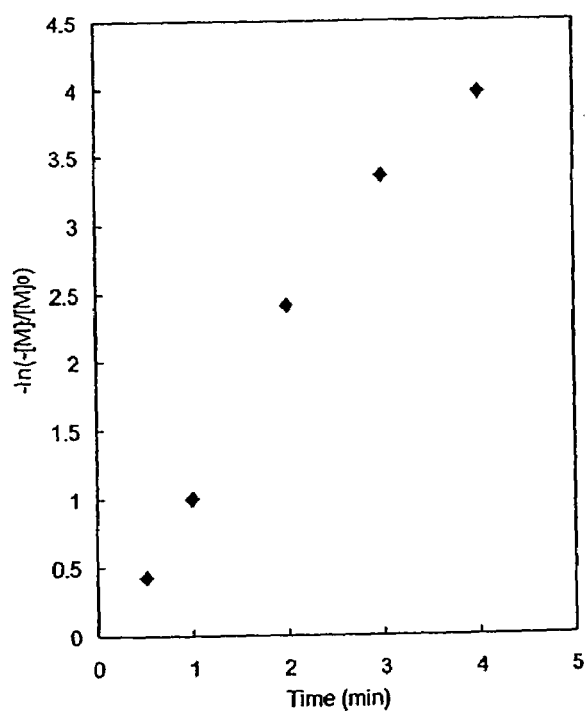
FIG. 6 is a graph showing bulk polymerization kinetics of 1,4-benzodioxepin-3-methyl-2,5-dione. Polymerization conditions: 130° C., [monomer]: [DMAP]: [1-phenylethanol]= 100:2:1.
Figure 7:
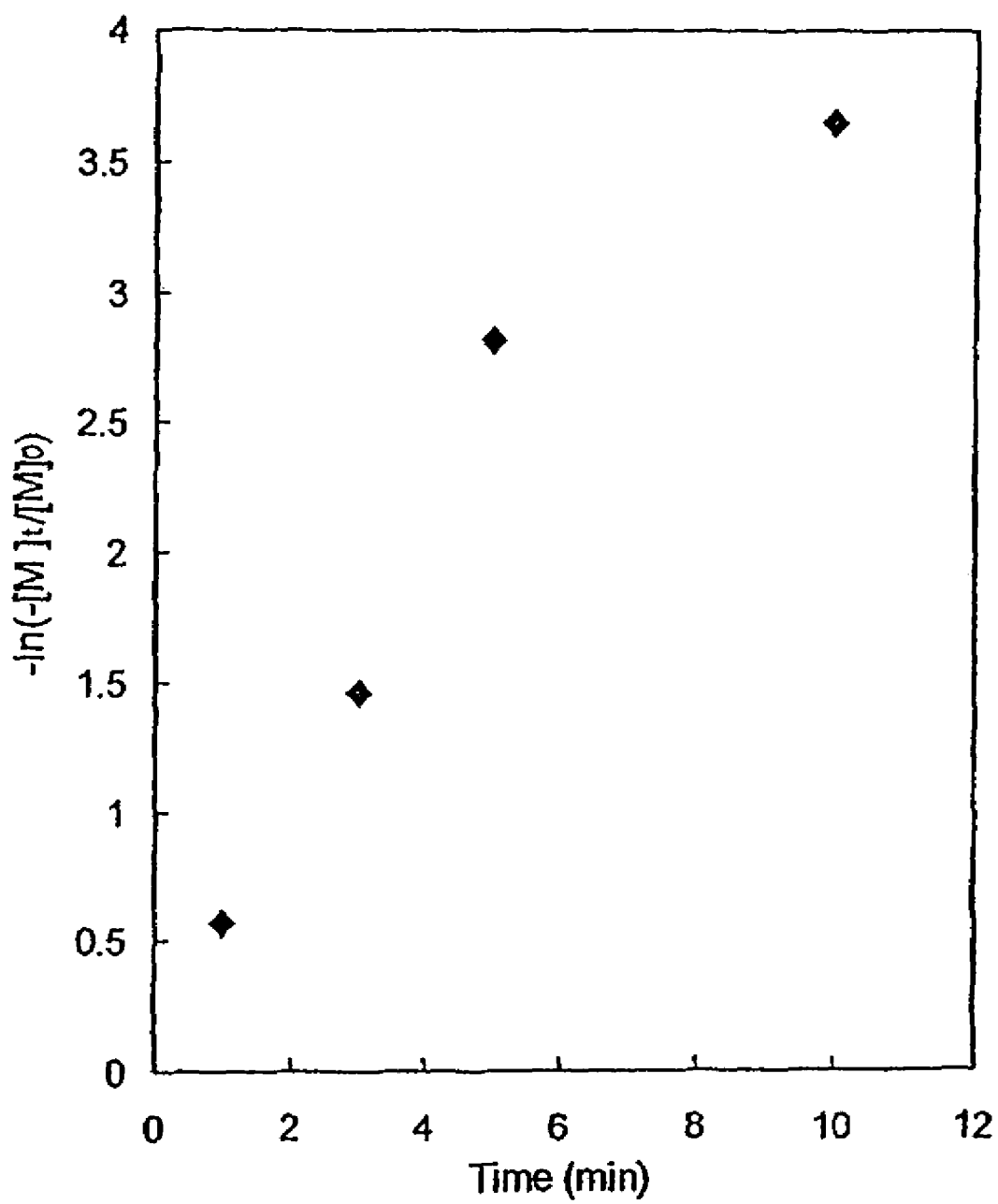
FIG. 7 is a graph showing bulk polymerization kinetics of 1,4-benzodioxepin-3-cyclohexyl-2,5-dione. Polymerization conditions: 160° C., [monomer]: [DMAP]: [1-phenylethanol]=100:2:1.

As noted earlier for the bulk polymerization of dicyclohexylglycolide, high temperature runs may introduce complications, such as that high polymerization rates make collecting data at low conversions problematic and the polymerization-depolymerization equilibrium might need to be taken into account in the kinetic analysis because of high conversions ([17]A. Duda, A. Kowalski, J. Libiszowski, and S. Penczek, *Macromol. Symp.* 2005, 224, 71-83); and ([22]Witzke, D. R.; Narayan, R.; Kolstad, J. J. *Macromolecules* 1997, 30, 7075-7085). However, the bulk polymerization kinetics of 1,4-benzodioxepin-3-methyl-2,5-dione and 1,4-benzodioxepin-3-cyclohexyl-2,5-dione followed the first-order reaction pretty well even under relatively high conversions (FIG. 6 and FIG. 7).

Figure 8:
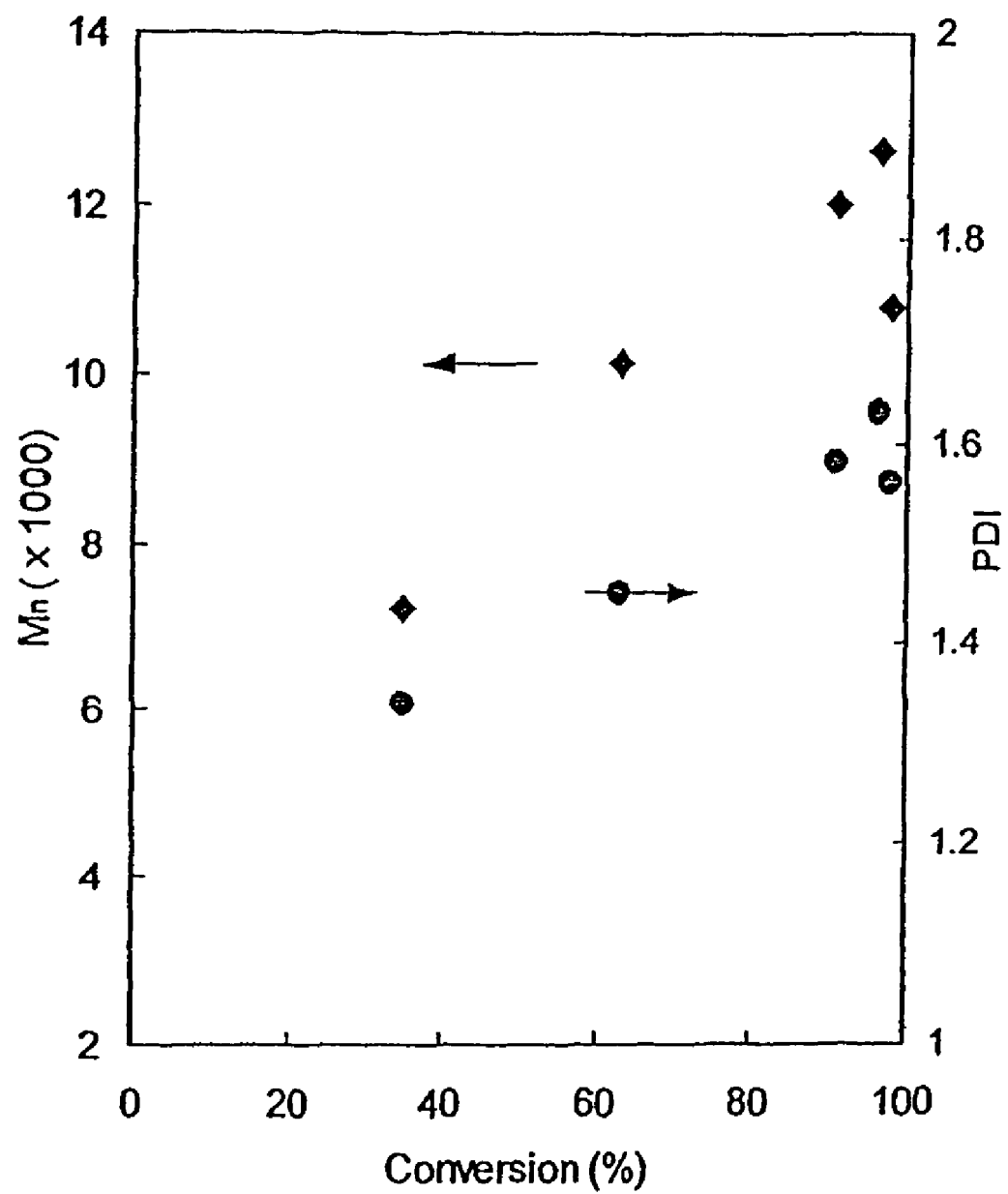
FIG. 8 is a graph showing evolution of the molecular weight (♦) and polydispersity (●) with conversion for the bulk polymerization of 1,4-benzodioxepin-3-methyl-2,5-dione. Polymerization conditions: 130° C., [monomer]: [DMAP]:[1-phenylethanol]=100:2:1.
Figure 9:
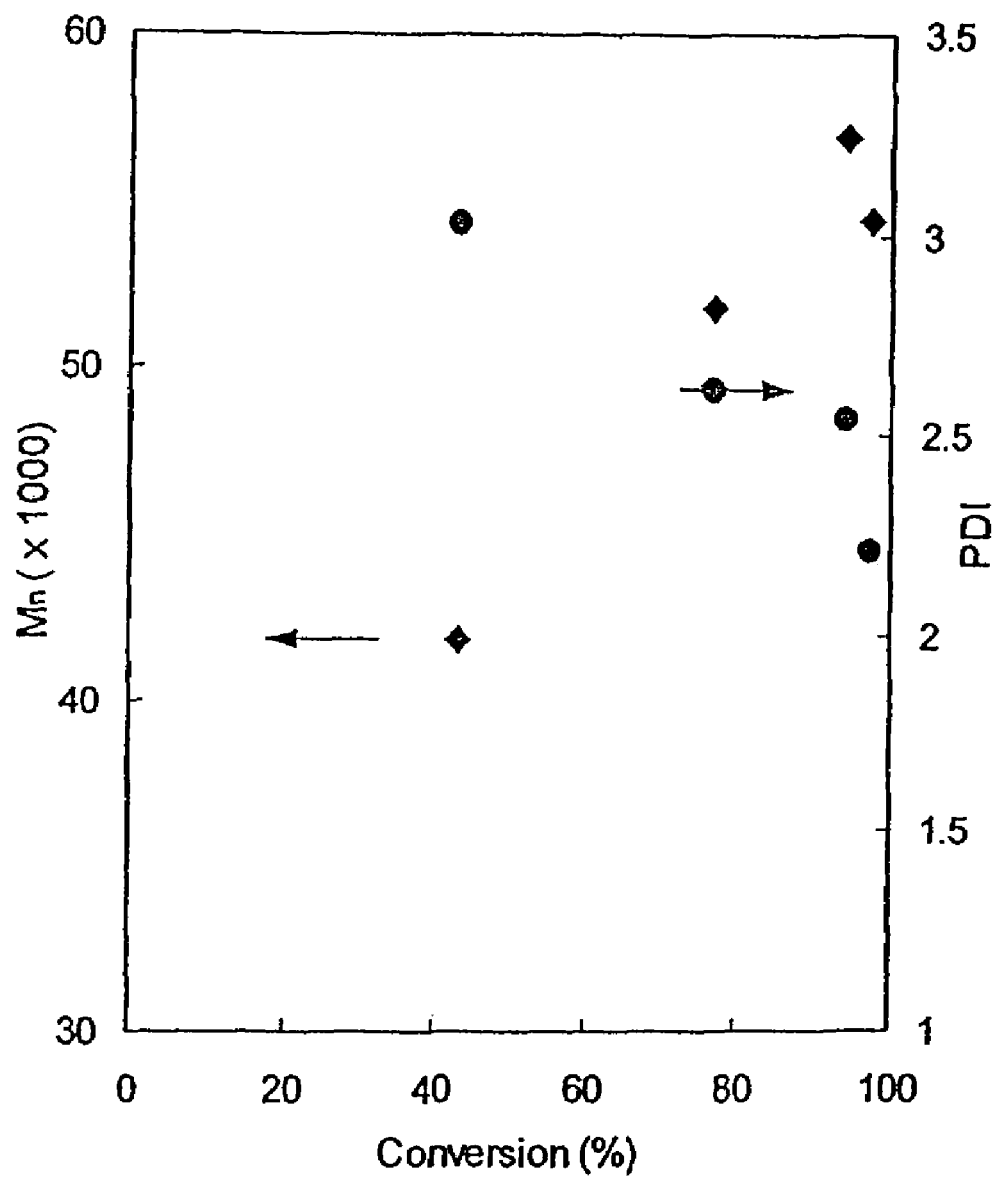
FIG. 9 is a graph showing evolution of the molecular weight (♦) and polydispersity (●) with conversion for the bulk polymerization of 1,4-benzodioxepin-3-cyclohexyl-2,5-dione. Polymerization conditions: 160° C., [monomer]: [DMAP]: [1-phenylethanol]=100:2:1.

The evolution of the number-average molecular weight ($M_n$) and polydispersity (PDI) with conversion in the polymerization of 1,4-benzodioxepin-3-methyl-2,5-dione and 1,4-benzodioxepin-3-cyclohexyl-2,5-dione are shown in FIG. 8 and FIG. 9 respectively. As the monomer conversion increases during bulk polymerization, $M_n$ increases, reaches a maximum at high conversion, and then drops down. This behavior is consistent with the mechanism for ring-opening polymerization of lactides ([23]Yin, M.; Baker, G. L. *Macromolecules* 1999, 32, 7711-7718). At low conversion, $M_n$ increases linearly with conversion because of the "living" nature of the ring-opening polymerization. When the monomer is nearly consumed, transesterification becomes competitive with propagation. While the intermolecular transesterification won't affect $M_n$, the formation of cyclic esters via intramolecular transesterification causes a reduction in $M_n$. Polydispersities are fairly high for these living polymerizations, probably because of extensive intermolecular and intramolecular transesterifications.

Figure 10:
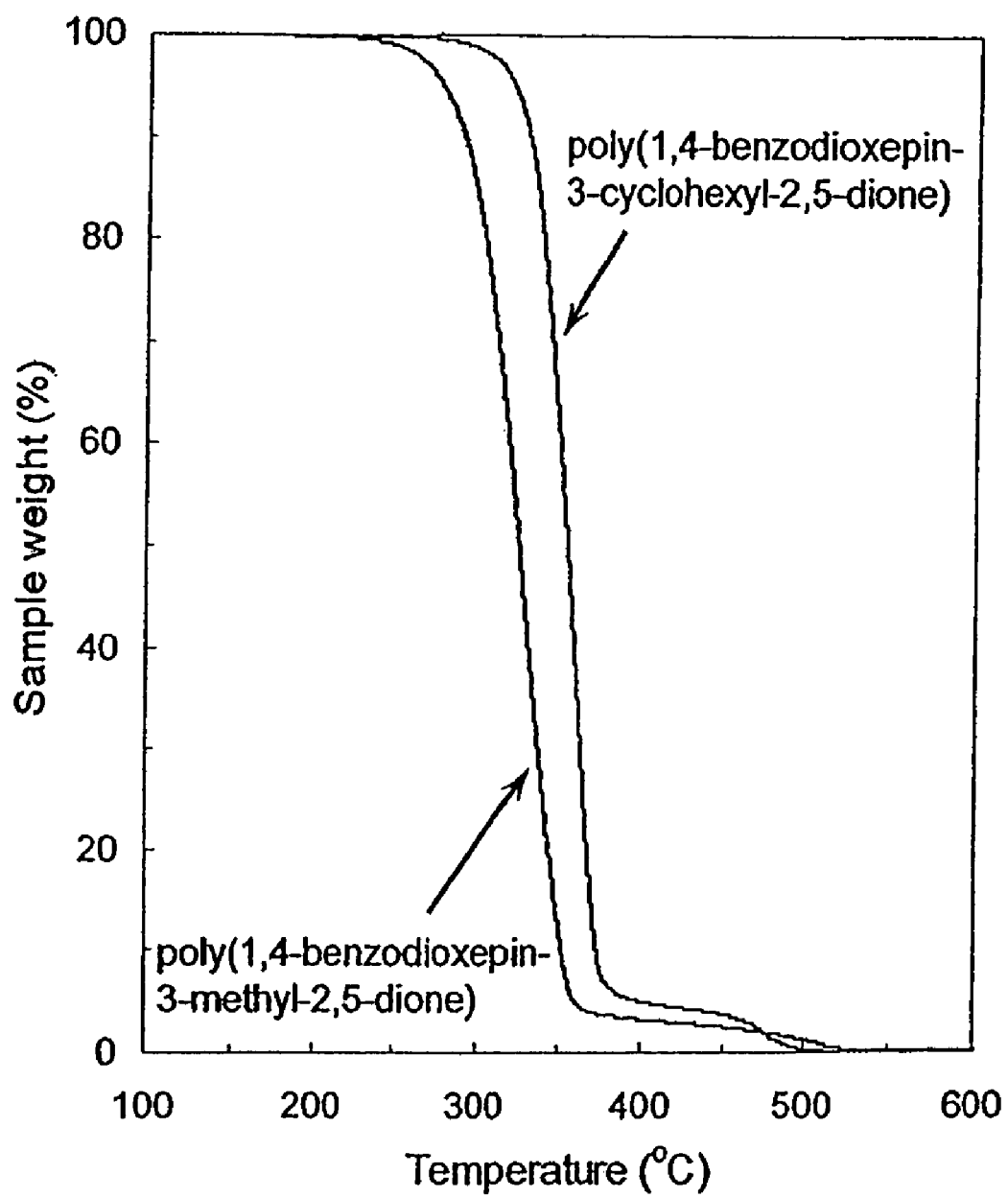
FIG. 10 is a graph showing thermogravimetric analysis results for poly(1,4-benzodioxepin-3-alkyl-2,5-dione). Samples were run in air at a heating rate of 10° C./min.

Polymer Properties of poly(1,4-benzodioxepin-3-alkyl-2,5-dione)s. The decomposition temperatures of polymers measured using thermogravimetric analysis (TGA) define the limiting use temperatures of the polymers. As shown in FIG. 10, the TGA trace for poly(1,4-benzodioxepin-3-cyclohexyl-2,5-dione) is similar to that of polylactides with onsets for weight loss near 300° C. followed by nearly complete weight loss. But the onset temperature for weight loss of poly(1,4-benzodioxepin-3-methyl-2,5-dione) is lot lower, only at around 230° C. This is probably due to its much lower molecular weight.

Figure 11:
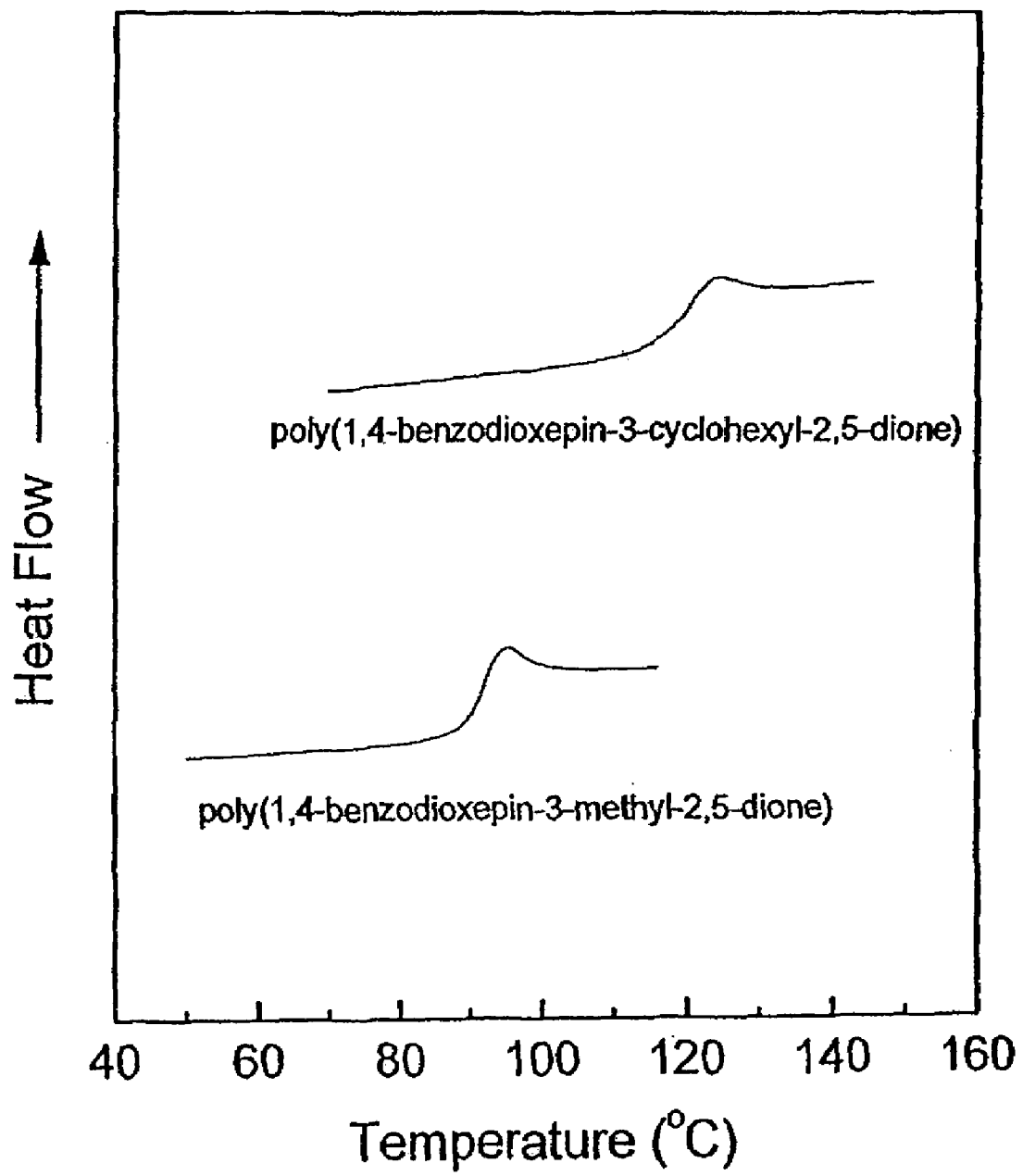
FIG. 11 is a graph showing DSC analyses of poly(1,4-benzodioxepin-3-alkyl-2,5-dione). Heating rate: 10° C./min under nitrogen. The data are second heating scans, taken after flash quenching from 150° C.
Figure 12:
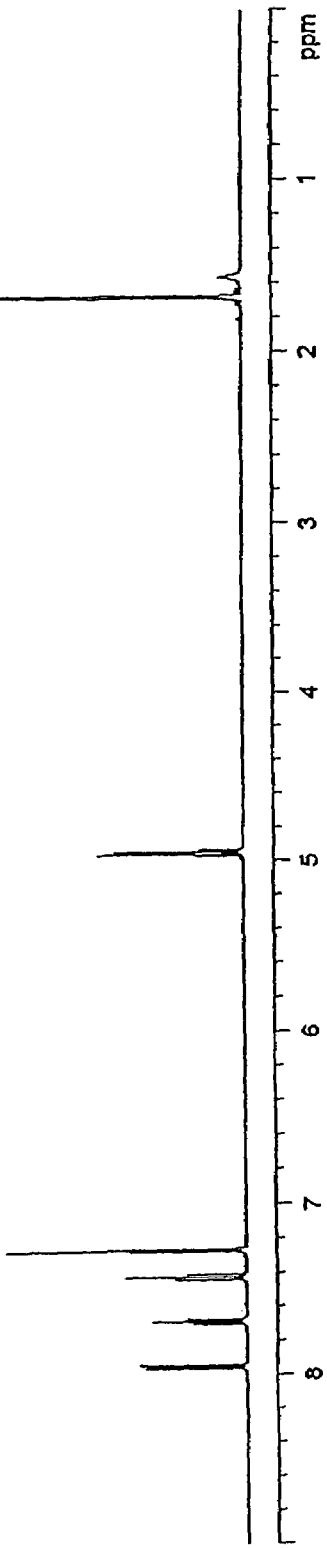
FIG. 12 is a graph showing $^1$H NMR spectrum of 1,4-benzodioxepin-3-methyl-2,5-dione.
Figure 13:
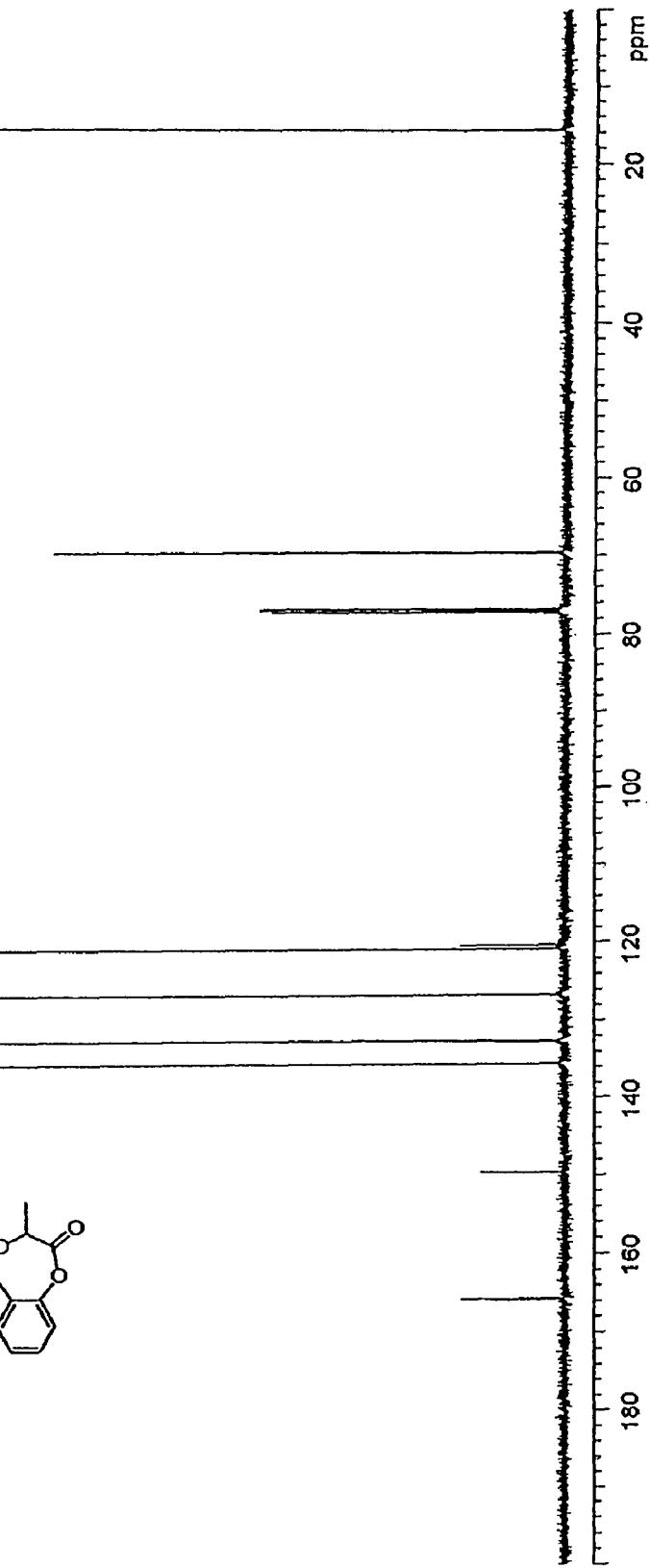
FIG. 13 is a graph showing $^{13}$C NMR spectrum of 1,4-benzodioxepin-3-methyl-2,5-dione.
Figure 14:
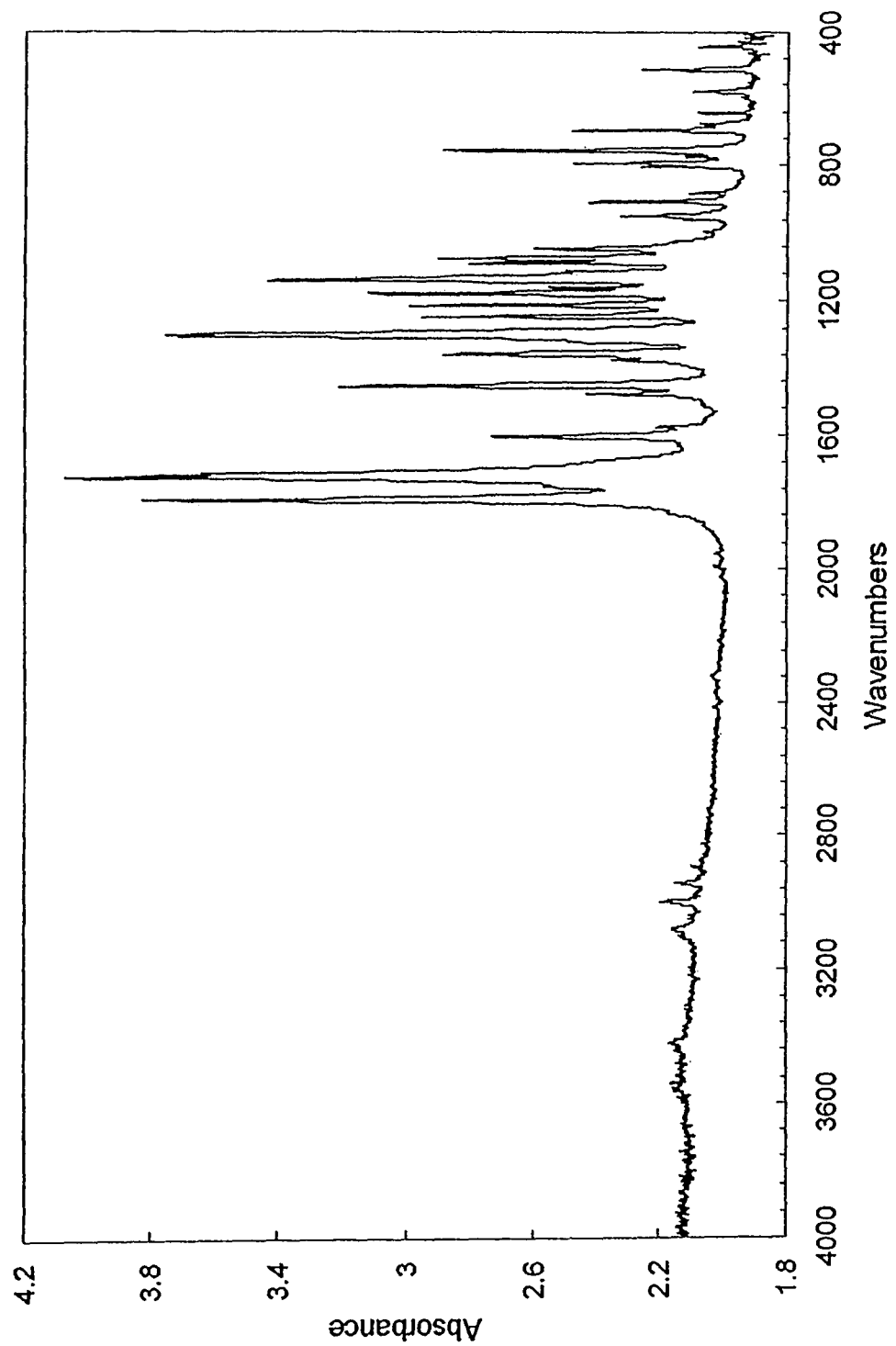
FIG. 14 is a graph showing FT-IR spectrum of 1,4-benzodioxepin-3-methyl-2,5-dione.
Figure 15:
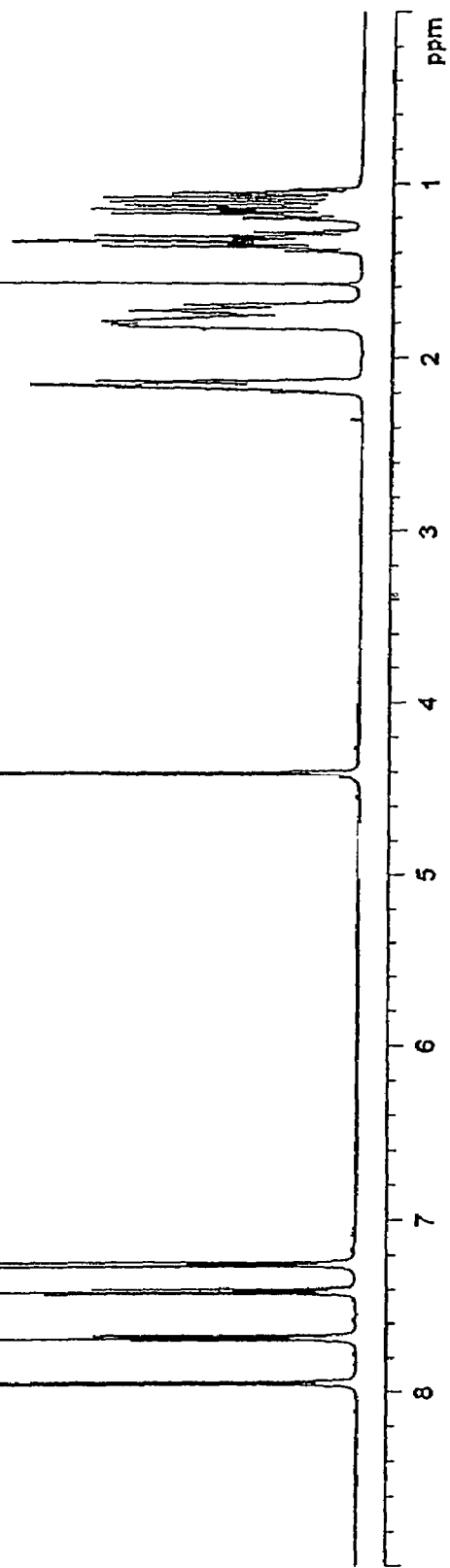
FIG. 15 is a graph showing $^1$H NMR spectrum of 1,4-benzodioxepin-3-cyclohexyl-2,5-dione.
Figure 16:
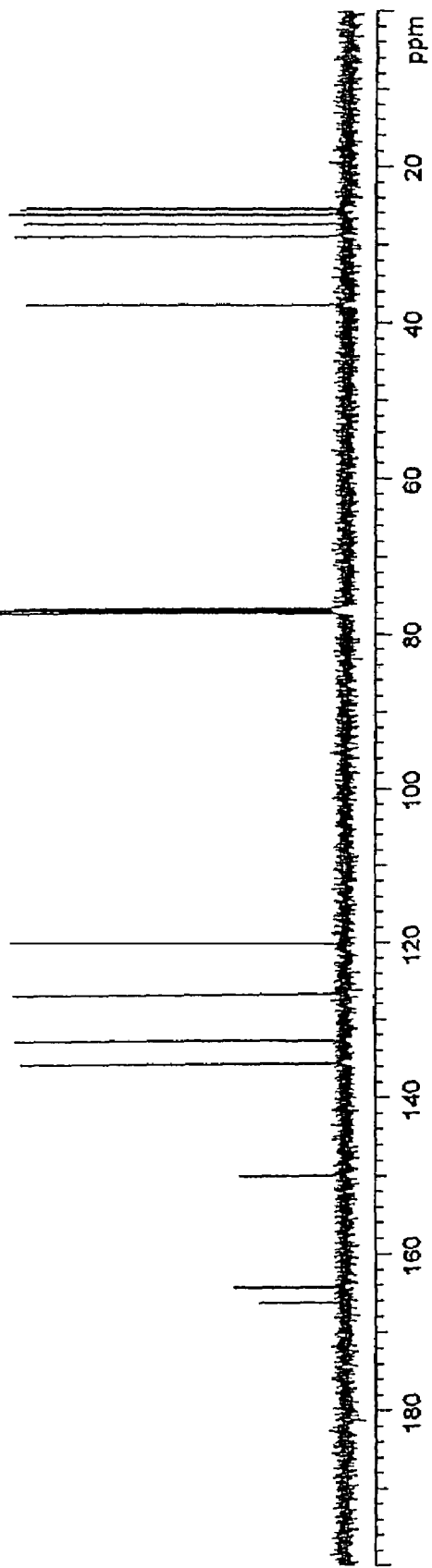
FIG. 16 is a graph showing $^{13}$C NMR spectrum of 1,4-benzodioxepin-3-cyclohexyl-2,5-dione.
Figure 17:
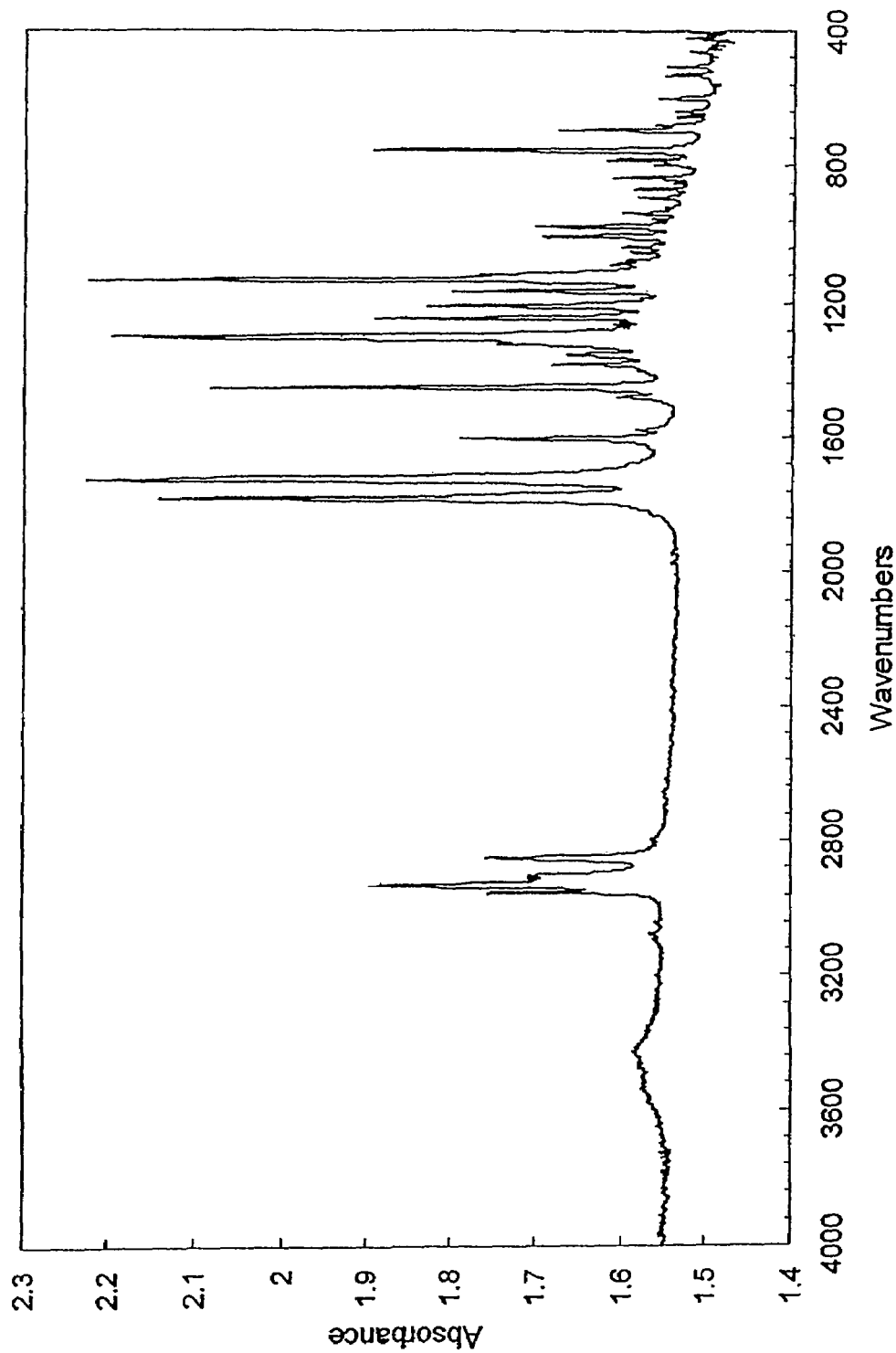
FIG. 17 is a graph showing FT-IR spectrum of 1,4-benzodioxepin-3-cyclohexyl-2,5-dione.
Figure 18:
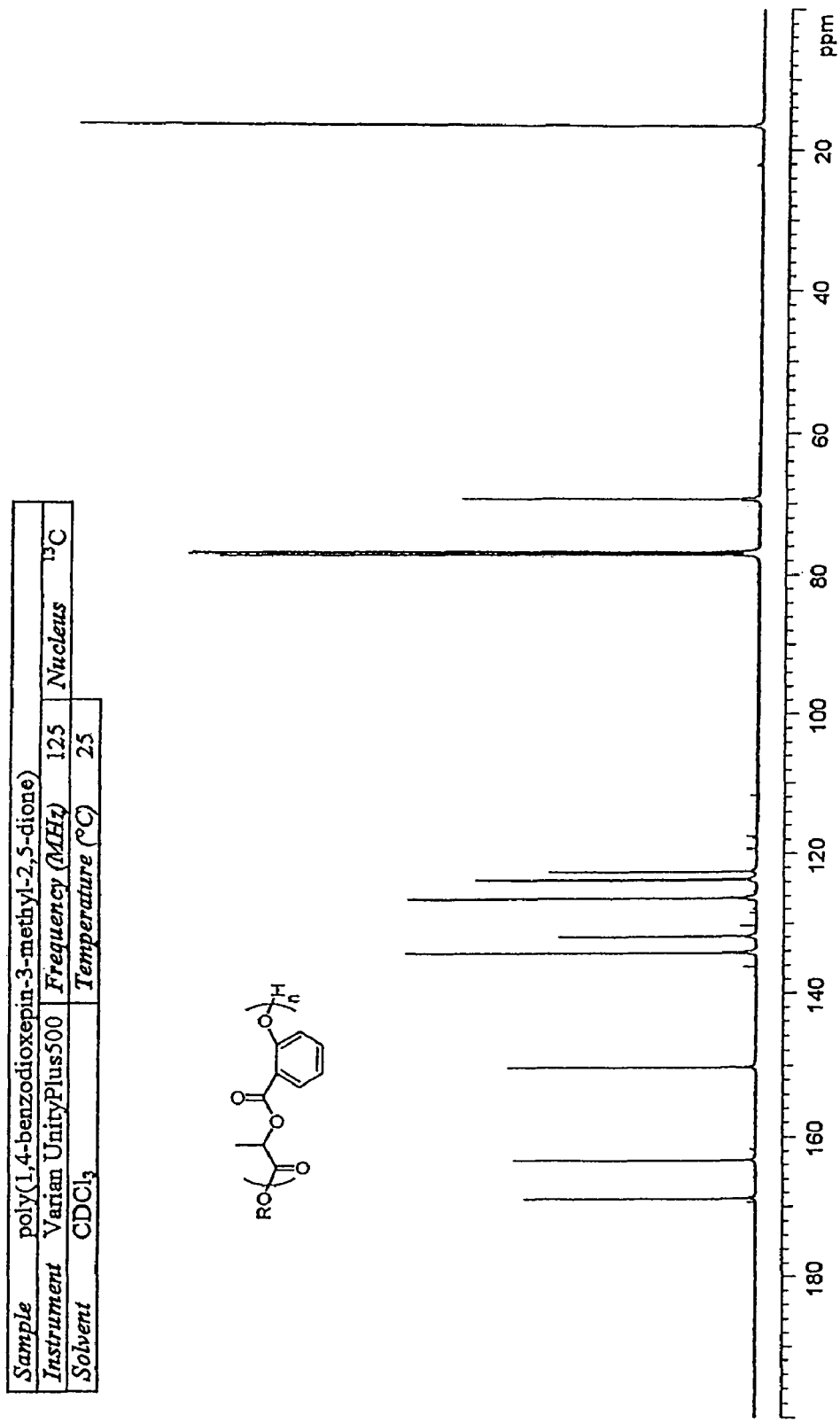
FIG. 18 is a graph showing $^{13}$C NMR spectrum of poly(1, 4-benzodioxepin-3-methyl-2,5-dione.
Figure 19:
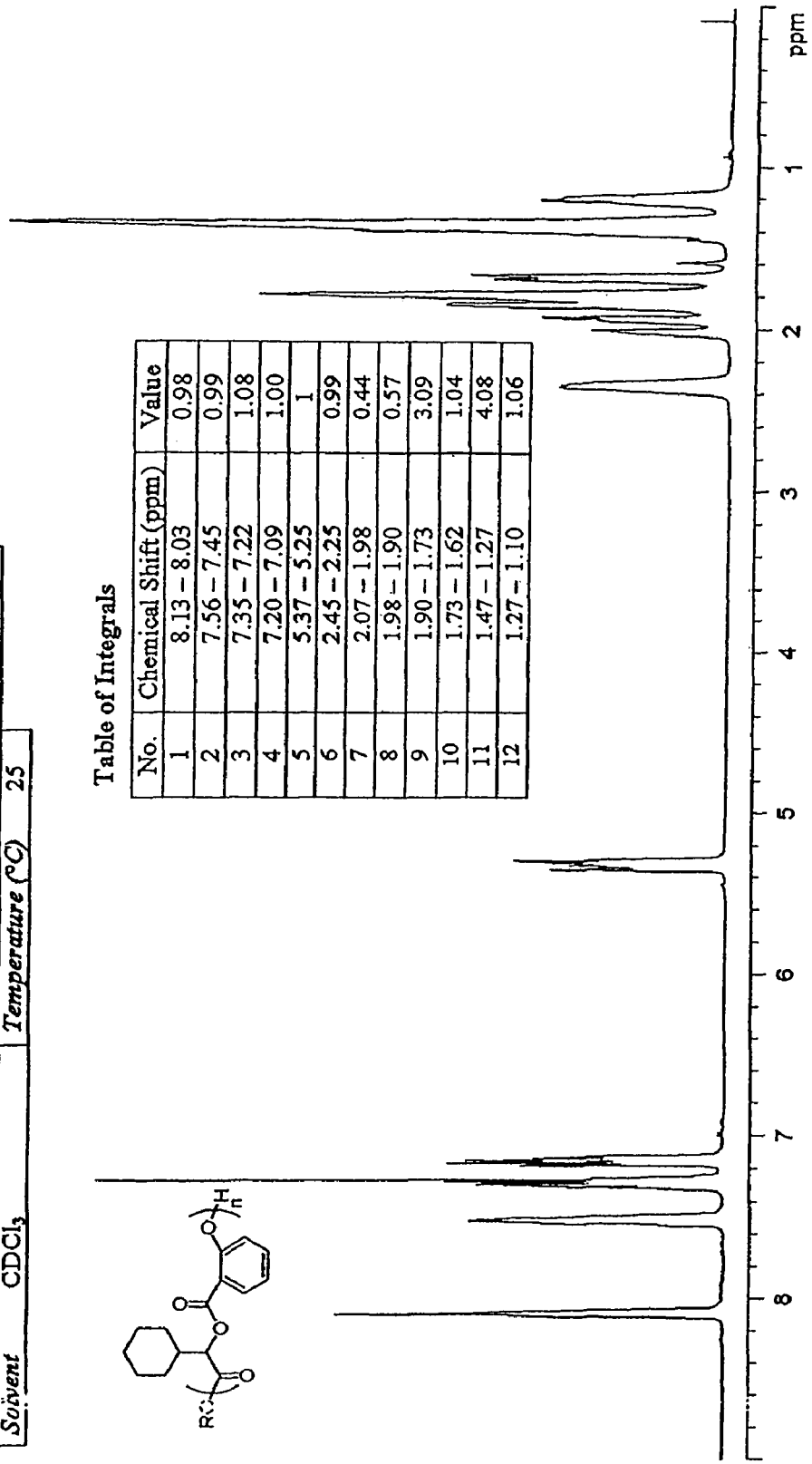
FIG. 19 is a graph showing $^1$H NMR spectrum of poly(1, 4-benzodioxepin-3-cyclohexyl-2,5-dione.
Figure 20:
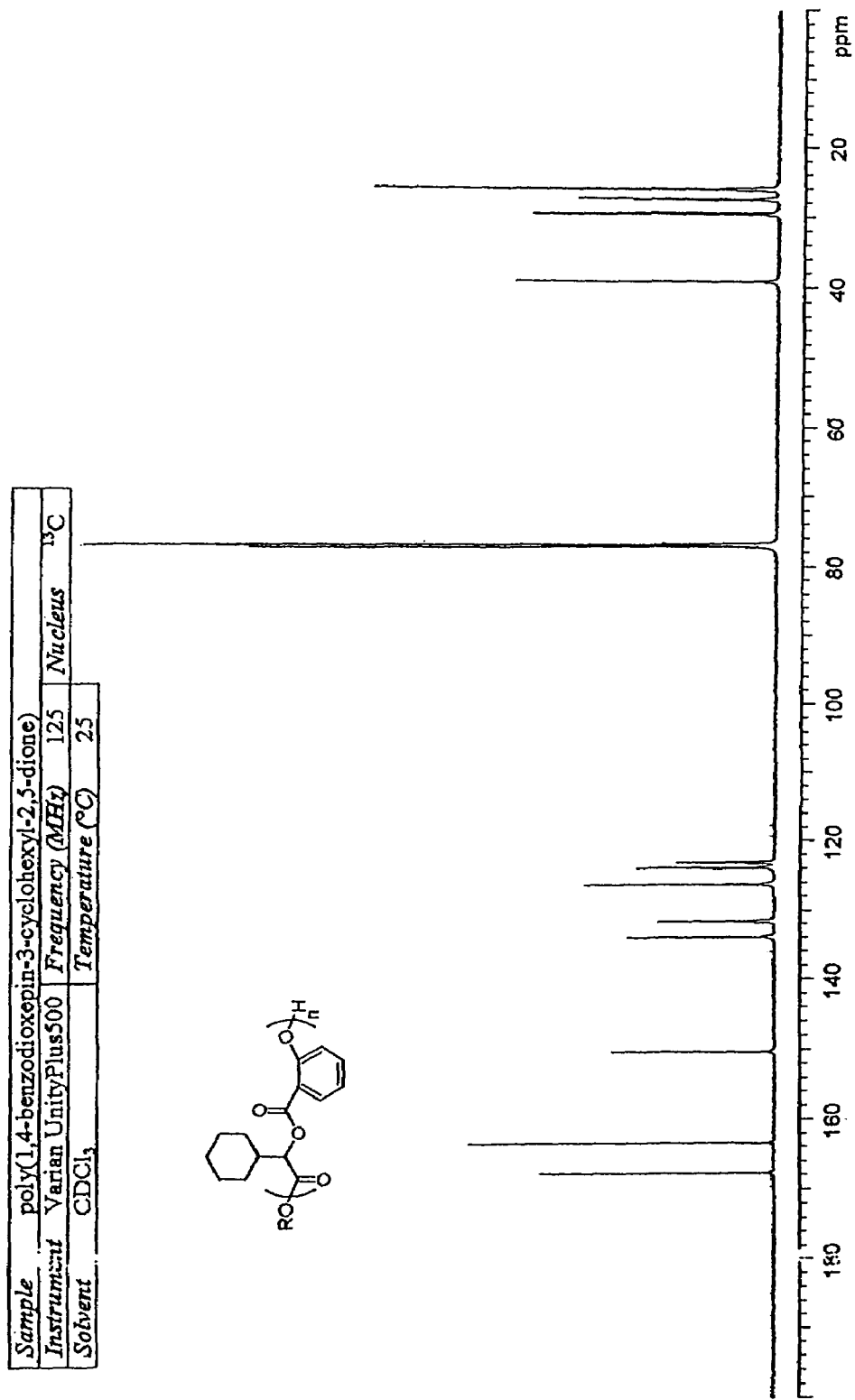
FIG. 20 is a graph showing $^{13}$C NMR spectrum of poly(1, 4-benzodioxepin-3-cyclohexyl-2,5-dione.

Glass transition temperatures measured by DSC are shown in Table 3 and FIG. 11. In agreement with the argument that incorporating aromatic rings into polymer backbone would increase the rotation barriers of polymers and hence $T_g$, poly(1,4-benzodioxepin-3-methyl-2,5-dione) has a very high $T_g$ (92° C.), which is comparable to that of poly(dicyclohexylglycolide). By further increasing the steric hindrance of side chains, poly(1,4-benzodioxepin-3-cyclohexyl-2,5-dione) shows an exceptionally high $T_g$ at 120° C. Because only racemic monomers were used, both polymers are amorphous (no melting transition), showing them as promising replacements for polystyrene.

TABLE 3

Properties of poly(1,4-benzodioxepin-3-alkyl-2,5-dione)s

| Polymer | $M_n$ | $M_w/M_n$ | $T_g$ (° C.) |
|---|---|---|---|
| Poly(1,4-benzodioxepin-3-methyl-2,5-dione)$^a$ | 10,500 | 1.50 | 92 |
| Poly(1,4-benzodioxepin-3-cyclohexyl-2,5-dione)$^b$ | 61,900 | 1.96 | 120 |

$^a$bulk polymerized at 130° C.;
$^b$bulk polymerized at 160° C.

Experimental Section

Unless otherwise specified, ACS reagent grade starting materials and solvents were used as received from commercial suppliers without further purification. $^1$H NMR analyses were carried out at room temperature on a Varian UntiyPlus-500 spectrometer at 500 MHz with the chemical shifts referenced to signals from residual protons in the solvent. $^{13}$C NMR spectra were obtained on a Varian UnityPlus-500 at 125 MHz. IR spectra were taken with Mattson Galaxy 3000 FT-IR. Elemental analyses were determined using a Perkin-Elmer 2400 CHNS/O Analyzer. Mass spectral analyses were carried out on a VG Masslab Trio-1. Melting points were taken on a Electrothermal capillary melting point apparatus and are uncorrected.

1,4-Benzodioxepin-3-methyl-2,5-dione. To a 500 mL 3-neck flask were added 27.6 g (0.2 mol) of salicylic acid, 0.23 mol of 2-bromopropionyl bromide, and 300 mL THF. The flask was purged with nitrogen and then cooled in a NaCl salt-ice bath. A mixture of 34.8 mL triethyl amine and 50 mL THF was added dropwise under mechanical stirring and the solution was cooled and stirred overnight. The solution was filtered to remove a white solid, and the filtrate was evaporated to dryness. The solid was dissolved in ethyl acetate. The solution was washed with 2 M HCl (3×100 mL), saturated NaCl, dried over MgSO$_4$, and then concentrated to give a pale pink crystal of the crude linear acid ester. The crystal was mixed with 1600 mL acetone and 67 g NaHCO$_3$, and refluxed for 2 hours. The solids were removed by filtration and the acetone was evaporated to dryness. The crude product was dissolved in dichloromethane, dried over MgSO$_4$, and dichloromethane was removed by rotary evaporation. The crude product was recrystallized from toluene once and benzene twice, and the white crystals were collected by filtration and dried under vacuum to give 9.66 g (25%) of 1,4-benzodioxepin-3-methyl-2,5-dione. $^1$H NMR (CDCl$_3$): δ (ppm) 7.95 (d, J=7.5 Hz, 1H), 7.68 (t, J=7.8 Hz, 1H), 7.42 (t, J=7.6 Hz, 1H), 7.26 (d, J=8.3 Hz, 1H), 4.94 (q, J=6.4 Hz, 1H), 1.68 (d, J=6.5 Hz, 3H). $^{13}$C NMR (CDCl$_3$): δ (ppm) 165.81, 165.61, 149.66, 135.53, 132.56, 126.69, 120.79, 120.25, 69.64, 15.63. IR (KBr): ν (cm$^{-1}$) 3085, 2998, 2944, 1788, 1718, 1604, 1454, 1302, 1247, 1213, 1176, 1138, 1073. Anal. Calcd. for C$_{10}$H$_8$O$_4$: C, 62.50; H, 4.20. Found: C, 62.37; H, 7.16. MS (EI) m/z 192.1 (3.7), 164.0 (10), 121.1 (10), 120.0 (100), 92.0 (45), 64.1 (12), 62.9 (19). mp 118-119° C.

1,4-Benzodioxepin-3-cyclohexyl-2,5-dione. To a solution of 200 mL methanol were added 27.2 g phenylacetic acid, 2.5 mL acetic acid, and 7.5 g rhodium on alumina (5%, Engelhard 5864). The mixture was sealed in an autoclave, purged with nitrogen, and then filled with hydrogen gas. Hydrogenation was carried out at room temperature for 8 hours under 1400 psi. The reaction mixture was then removed from the autoclave and filtered. The filtrate was concentrated to give 28.0 g (98%) crude 2-cyclohexylacetic acid. The crude acid was used directly without further purification. To a 500 mL 3-neck flask were added 85.7 g (0.6 mol) of 2-cyclohexylacetic acid, 86 mL thionyl chloride (1.2 mol), and a magnetic stir bar. The solution was stirred first at room temperature for 1 hour, and then at 85° C. for 1 hour. 38 mL bromine (0.75 mol) was added dropwise over 30 minutes, and the solution was stirred overnight at 85° C. The solution was vacuum distilled to give 2-cyclohexyl-2-bromoacetyl chloride as a bright pale yellow liquid. To a 500 mL 3-neck flask were added 27.6 g (0.2 mol) of salicylic acid, 55.1 g (0.23 mol) of 2-cyclohexyl-2-bromoacetyl chloride, and 300 mL THF. The flask was purged with nitrogen and then cooled in a NaCl salt-ice bath. A mixture of 34.8 mL triethyl amine and 50 mL THF was added dropwise under mechanical stirring and the solution was cooled and stirred overnight. The solution was filtered to remove a white solid, and the filtrate was evaporated to dryness. The solid was dissolved in ethyl acetate. The solution was washed with 2 M HCl (3×100 mL), saturated NaCl, dried over MgSO$_4$, and then concentrated to give a pale yellow crystal of the crude linear acid ester. 17.1 g of the acid ester intermediate was mixed with 400 mL THF and 10.5 mL (0.075 mol) triethyl amine, and refluxed overnight. The solids were removed by filtration and the THF was evaporated to dryness. The crude product was dissolved in ethyl acetate, washed with 2 M HCl (3×100 mL), saturated NaCl, dried over MgSO$_4$, and the ethyl acetate was removed by rotary evaporation. The crude product was recrystallized from toluene twice, and the needle-like colorless crystals were collected by filtration and dried under vacuum to give 5.85 g (45%) of 1,4-benzodioxepin-3-cyclohexyl-2,5-dione. $^1$H NMR (CDCl$_3$): δ (ppm) 7.94 (d, J=7.8 Hz, 1H), 7.68 (t, J=7.9 Hz, 1H), 7.41 (t, J=7.6 Hz, 1H), 7.25 (d, J=8.3 Hz, 1H), 4.40 (d, J=7.6 Hz, 1H), 2.24-2.08 (m, 2H), 1.88-1.65 (m, 4H), 1.42-1.25 (m, 2H), 1.24-0.99 (m, 3H). $^{13}$C NMR (CDCl$_3$): δ (ppm) 166.03, 164.11, 149.82, 135.48, 132.56, 126.55, 120.72, 120.11, 76.53, 37.70, 28.90, 27.28, 26.07, 25.51, 25.33. IR (KBr): ν (cm$^{-1}$) 3074, 2954, 2933, 2851, 1783, 1729, 1606, 1453, 1297, 1247, 1212, 1133. Anal. Calcd. for C$_{15}$H$_{16}$O$_4$: C, 69.22; H, 6.20. Found: C, 69.28; H, 6.17. MS (EI) m/z 260.1 (0.3), 232.1 (2.9), 149.0 (10), 120.0 (100), 92.0 (33). mp 156-157° C.

Solution polymerization of 1,4-benzodioxepin-3-alkyl-2,5-diones. A Schlenk flask containing 2.0 mmol of 1,4-benzodioxepin-3-alkyl-2,5-dione and a magnetic stir bar was fitted with a septum and then evacuated and refilled with argon three times. Predetermined amounts of anhydrous toluene, and toluene solutions of 4-(dimethylamino)pyridine and 1-phenylethanol were then added via syringe through the septum to yield a 0.2 M monomer concentration. The Schlenk flask was then suspended in a 90° C. oil bath to initiate polymerization. For kinetic studies, aliquots of the reaction solution were removed by using a syringe at specific intervals and were analyzed by $^1$H NMR to determine the monomer conversion.

Bulk polymerization of 1,4-benzodioxepin-3-alkyl-2,5-diones. Solvent-free polymerizations were carried out in sealed ampoules prepared from ⅜ in. diameter glass tubing. After charging with the 1,4-benzodioxepin-3-alkyl-2,5-dione and a stir bar, the ampoule was connected to a vacuum line through a vacuum adapter. After evacuating the ampoule for 2 hours, it was filled with argon, and a syringe was used to add a predetermined amount of the 4-(dimethylamino)pyridine and 1-phenylethanol solutions (in toluene) to the ampoule through the adapter. The solvent was removed in vacuo, and the ampoule was flame-sealed and immersed in oil bath. At the end of the polymerization, the ampoule was cooled, opened, and the polymer was dissolved in dichloromethane. A portion of the solution was evacuated to dryness and analyzed by NMR for conversion. The rest of polymer solution was precipitated three times in cold methanol.

Polymer characterization. The molecular weights of polymers were determined by Gel Permeation Chromatography (GPC) using a PLgel 20 m Mixed A column and a Waters 2410 differential refractometer detector at 35° C. THF was used as the eluting solvent at a flow rate of 1 mL/min, and monodisperse polystyrene standards were used to calibrate the molecular weights. Differential Scaning Calorimetry (DSC) analyses of the polymers were obtained using a TA DSC Q100. Samples were run under a nitrogen atmosphere at a heating rate of 10° C./min, with the temperature calibrated with an indium standard. Thermogravimetric analyses (TGA) were run both in air and under nitrogen at a heating rate of 10° C./min using a Perkin-Elmer TGA 7. Atomic Force Microscopy (AFM) analyses of the polymer thin film where run at room temperature in non-contact mode (tapping mode) using Pacific Nanotechnology Nano-R AFM. Polymer thin films were prepared by spin-coating the polymer solution (4 mg/mL in THF) on the silicon wafer and vacuum dried at room temperature. The measurement was done with the lightest set point possible at a scanning rate of 0.85 Hz and oscillation frequency around 300 KHz.

Figures A2 to A9 show supporting information.

The referenced polymers can be produced from a combination of 1,4-benzodioxepin-3-cyclohexyl-2,5-dione and 1,4-benzodioxepin-3-methyl-2,5-dione to produce block polymers. This allows selection of particular properties. Copolymers can be produced from 1,4-benzodioxepin-3-cyclohexyl-2,5-dione and at least one of: a) glycolide, b) (L-) lactide, c) an alkylene carbonate, d) p-dioxanone, e) e-caprolactone, f) 1,4-dioxepan-2-one, or g) 1,5-dioxepan-2-one. The polymers can also be blended together.

The preferred comonomer components of the copolymers are glycolide and L-lactide, and the most preferred comonomer component is glycolide. The preferred amount of monomer from which the copolymers of this invention are prepared ranges from about 1 to about 35 weight percent, more preferably from about 5 to about 15 weight percent. The preferred alkylene carbonate comonomer component is trimethylene carbonate.

The polymers of the present invention are generally useful for applications where biodegradation is important. Surgical applications are important uses.

REFERENCES

1. Dechy-Cabaret, O.; Martin-Vaca, B.; Bourissou, D. *Chem. Rev.* 2004, 104, 6147-6176.
2. Lenz, R. W.; Marchessault, R. H. *Biomacromolecules* 2005, 6, 1-8.
3. Mecking, S. *Angewandte Chemie-International Edition* 2004, 43, 1078-1085.
4. Kint, D. P. R.; Munoz-Guerra, S. *Polym. Int.* 2003, 52, 321-336.
5. Nagahata, R.; Sugiyama, J.; Goyal, M.; Asai, M.; Ueda, M.; Takeuchi, K. *J. Polym. Sci., Part A: Polym. Chem.* 2000, 38, 3360-3368.
6. Nagahata, R.; Sugiyama, J. J.; Goyal, M.; Goto, M.; Honda, K.; Asai, M.; Ueda, M.; Takeuchi, K. *Polymer* 2001, 42, 1275-1279.
7. Youk, J. H.; Boulares, A.; Kambour, R. P.; MacKnight, W. J. *Macromolecules* 2000, 33, 3600-3605.
8. Schmeltzer, R. C.; Schmalenberg, K. E.; Uhrich, K. E. *Biomacromolecules* 2005, 6, 359-367.
9. Prudencio, A.; Schmeltzer, R. C.; Uhrich, K. E. *Macromolecules* 2005, 38, 6895-6901.
10. Schmeltzer, R. C.; Anastasiou, T. J.; Uhrich, K. E. *Polym. Bull.* 2003, 49, 441-448.
11. Anastasiou, T. J.; Uhrich, K. E. *J. Polym. Sci., Part A: Polym. Chem.* 2003, 41, 3667-3679.
12. Bedell, C.; Deng, M.; Anastasiou, T. J.; Uhrich, K. E. *J. Appl. Polym. Sci.* 2001, 80, 32-38.
13. Auras, R.; Harte, B.; Selke, S. *Macromol. Biosci.* 2004, 4, 835-864.
14. Liu, T. Q.; Simmons, T. L.; Baker, G. L. Polymeric Materials: Science & Engineering 2003, 88, 420.
15. Jing, F.; Smith, M. R.; Baker, G. L. *Polym. Prepr.* 2005, 46, 1006.
16. Kagan, F.; Birkenmeyer, R. D. *J. Am. Chem. Soc.* 1959, 81, 1986-1991.
17. A. Duda, A. Kowalski, J. Libiszowski, and S. Penczek, *Macromol. Symp.* 2005, 224, 71-83.
18. Fan, Y. J.; Nishida, H.; Shirai, Y.; Endo, T. *Polym. Degrad. Stab.* 2004, 84, 143.
19. Nishida, H.; Mori, T.; Hoshihara, S.; Fan, Y. J.; Shirai, Y.; Endo, T. *Polym. Degrad. Stab.* 2003, 81, 515.
20. Nederberg, F.; Connor, E. F.; Glausser, T.; Hedrick, J. L. *Chem. Commun.* 2001, 2066-2067.
21. Nederberg, F.; Connor, E. F.; Moller, M.; Glauser, T.; Hedrick, J. L. *Angewandte Chemie-International Edition* 2001, 40, 2712-2715.
22. Witzke, D. R.; Narayan, R.; Kolstad, J. J. *Macromolecules* 1997, 30, 7075-7085.
23. Yin, M.; Baker, G. L. *Macromolecules* 1999, 32, 7711-7718.
24. Aggarwal, V. K.; Thomas, A.; Schade, S. *Tetrahedron* 1997, 53, 16213-16228.
25. Masamune, S.; Choy, W.; Kerdesky, F. A. J.; Imperiali, B. *Journal of the American Chemical Society* 1981, 103, 1566-1568.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A homopolymer of a monomer represented by the following formula:

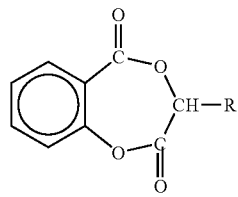

wherein R is cyclohexyl.

2. The homopolymer of claim 1 wherein the glass transition temperature of the homopolymer is about 120° C.

3. A surgical device prepared from the homopolymer of claim 1.

* * * * *